(12) United States Patent
Basilico et al.

(10) Patent No.: US 8,404,442 B2
(45) Date of Patent: Mar. 26, 2013

(54) METHODS FOR IDENTIFICATION OF BONE ANABOLIC AGENTS

(75) Inventors: Claudio Basilico, New York, NY (US);
Alka Mansukhani, New York, NY (US);
Upal Basu Roy, New York, NY (US)

(73) Assignee: New York University, New York, NY (US)

( * ) Notice: Subject to any disclaimer, the term of this patent is extended or adjusted under 35 U.S.C. 154(b) by 389 days.

(21) Appl. No.: 12/832,936

(22) Filed: Jul. 8, 2010

(65) Prior Publication Data

US 2011/0014620 A1    Jan. 20, 2011

Related U.S. Application Data

(60) Provisional application No. 61/270,506, filed on Jul. 8, 2009.

(51) Int. Cl.
*C12Q 1/68* (2006.01)
(52) U.S. Cl. ...................................................... 435/6.1
(58) Field of Classification Search .................. None
See application file for complete search history.

*Primary Examiner* — Christopher M. Babic
(74) *Attorney, Agent, or Firm* — Fish & Richardson P.C.

(57) ABSTRACT

The present invention is related to methods for identifying bone anabolic agents and factors, identifying pathways that promote proliferation of osteoblasts for bone growth and/or repair, and for identifying new therapeutic targets for treatments for osteoporosis and other bone degenerative disorders characterized by osteopenia.

19 Claims, 9 Drawing Sheets

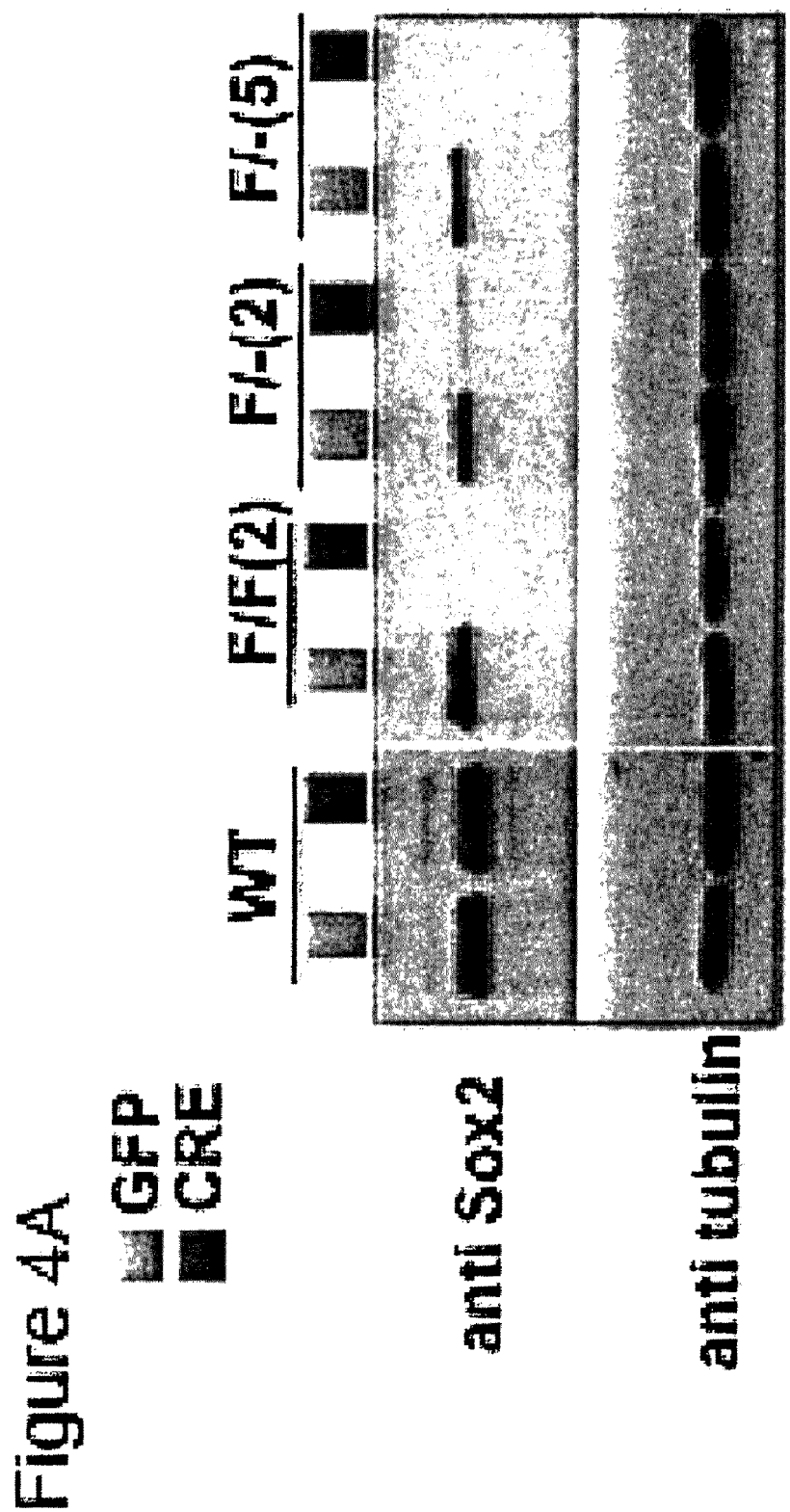

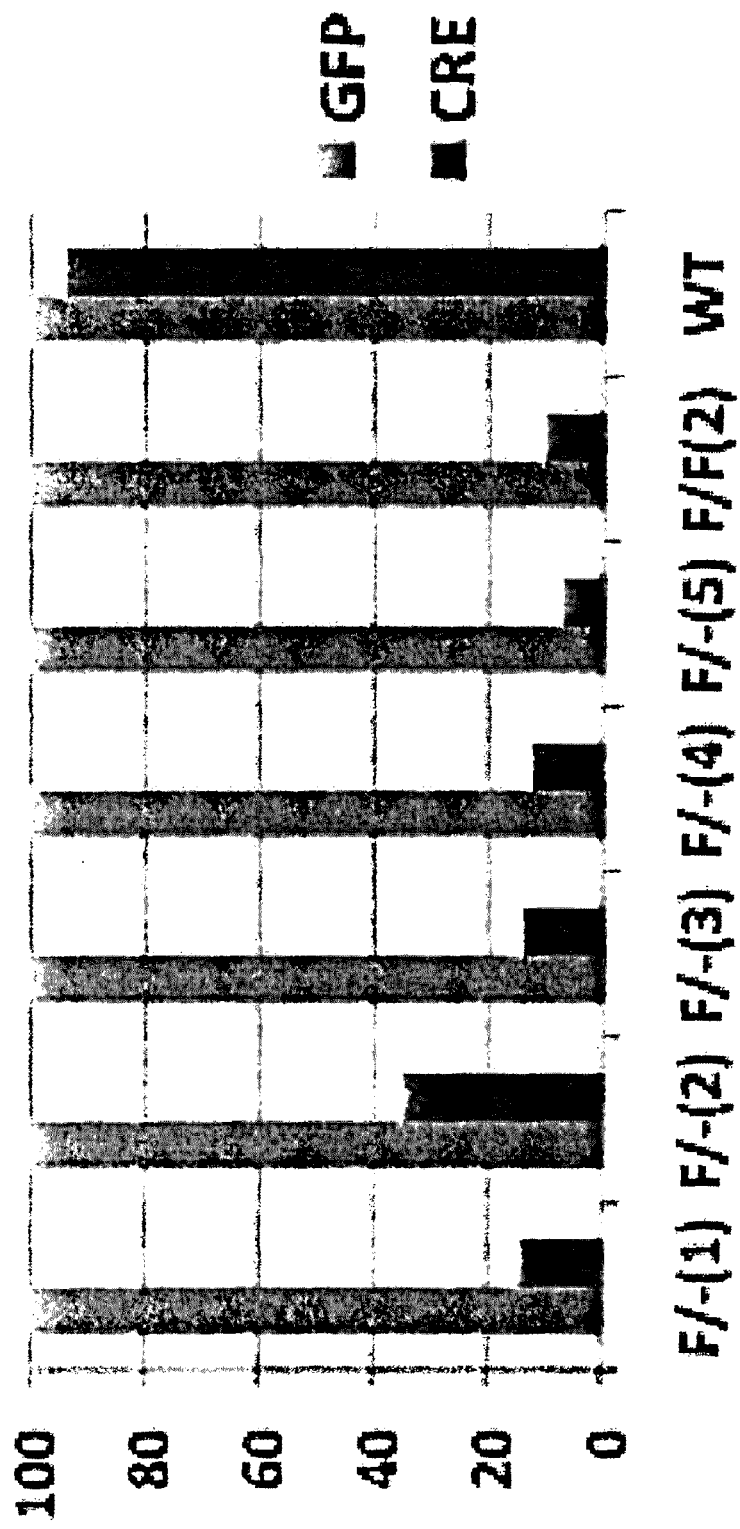

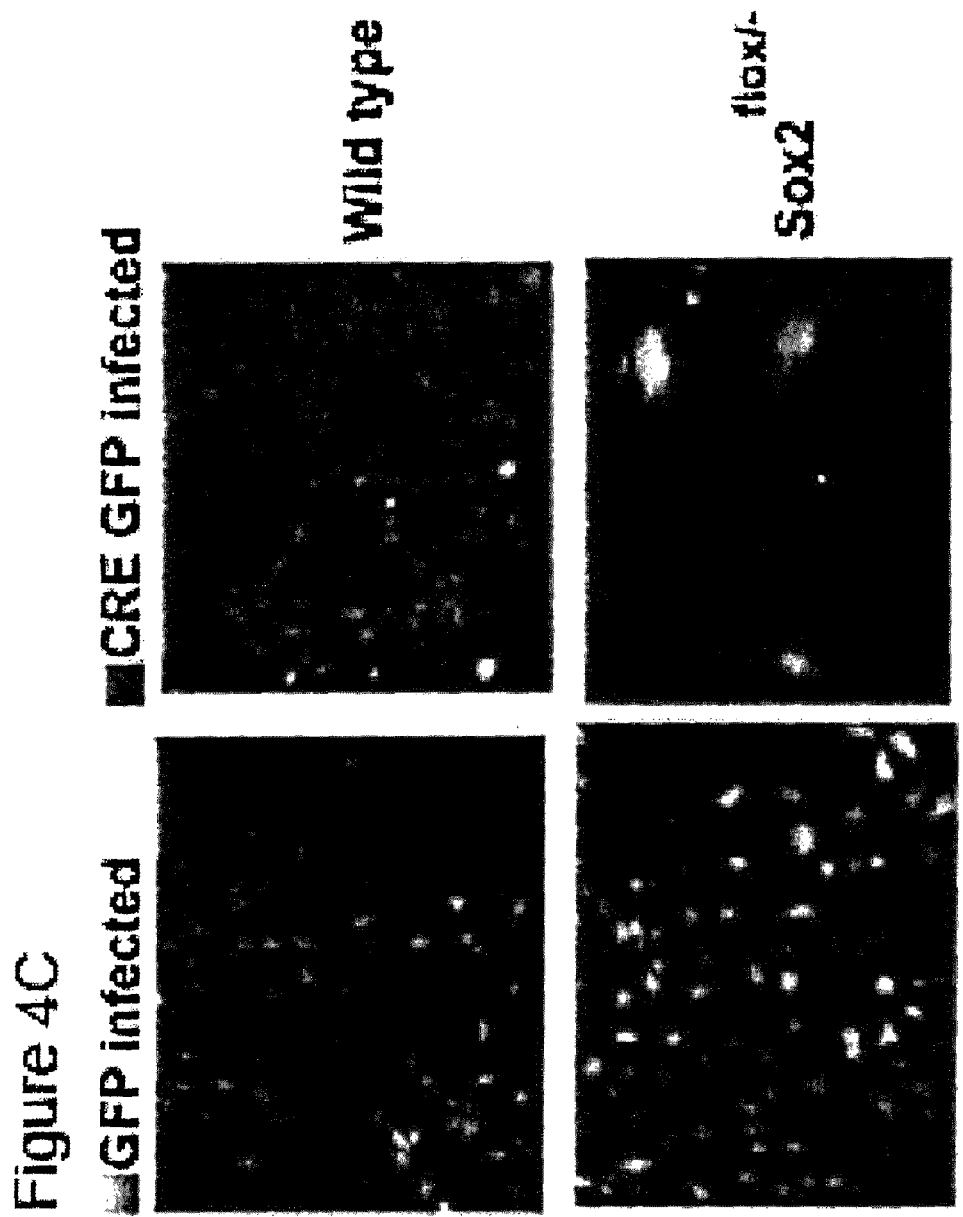

METHODS FOR IDENTIFICATION OF BONE ANABOLIC AGENTS

This application claims priority under 35 U.S.C. §119(e) from Provisional Application Ser. No. 61/270,506 filed on Jul. 8, 2009. The entire disclosure of said application is hereby incorporated by reference in its entirety.

The United States Government has certain rights to this invention by virtue of funding received from the National Institute of Health, Department of Health and Human Services, Grant No. 2R01AR05/358.

FIELD OF THE INVENTION

The present invention is related to methods for identifying bone anabolic agents and factors, identifying pathways that promote proliferation of osteoblasts for bone growth and/or repair, and for identifying new therapeutic targets for treatments for osteoporosis and other bone degenerative disorders characterized by osteopenia.

BACKGROUND OF THE INVENTION

Bone formation relies on the interaction of various cell types, but it is cells of the osteoblast lineage that are responsible for synthesis, deposition and mineralization of matrix (23). Bone is formed of two types of osseous tissue; compact bone and trabecular bone. Compared to compact bone, trabecular bone has a higher surface area but is less dense, softer, weaker, and less stiff. The primary anatomical and functional unit of trabecular bone is the trabecula. A trabecula is a small, often microscopic, tissue element in the form of a small beam, strut or rod, generally having a mechanical function. On histological section, a trabecula can look like a septum, but in three dimensions they are topologically distinct, with trabeculae being roughly rod or pillar-shaped and septa being sheet-like. Trabecular bone typically occupies the interior region of bones. Trabecular bone is highly vascular and frequently contains red bone marrow where hematopoiesis, which is the production of blood cells, occurs.

The study of bone formation and the factors and mechanisms that regulate this process are often studied in vitro. Studies using primary osteoblast cultures are often used, but immortalized osteoblastic cell lines can also be used. The most extensively studied primary osteoblast cultures are derived from calvaria (skull) or by differentiation of bone marrow-derived mesenchymal stem cells (MSCs).

MSCs from bone marrow have the capacity to differentiate into cells of the connective tissue lineage including bone, fat, cartilage and muscle (23). Calvarial osteoblasts are derived from the differentiation of mesenchymal cells, which have also been reported to be multipotent; it has been demonstrated that they also have the potential to enter the chondrogenic and adipogenic lineages (24). Cultured embryonic and newborn murine calvarial cells are usually a mixed population of MSCs, osteoprogenitors and osteoblasts, and the relative amounts of these different populations depends on the age of the calvaria and the culture conditions (25). However, the signals that regulate the potency, expansion, and commitment of mesenchymal stem cells of the osteoblast lineage remain to be defined.

Understanding the mechanisms that regulate and enhance bone anabolic processes (bone growth) is critical for developing treatments for a number of conditions and diseases of the bone. For example, osteoporosis is a disease of the bone that affects approximately 8 million women and 2 million men in the United States. Osteoporosis is a disease of the bone in which the amount of bone is decreased and the strength of trabecular bone is reduced, cortical bone becomes thin and bones are susceptible to fracture. Osteoporosis is a condition that features loss of the normal density of bone and occurs most often in older people and post-menopausal women (26, 30). Current treatments of osteoporosis include calcium supplementation and different classes of osteoclast inhibitors, such as bisphosphonates. However, these treatments can have unwanted side effects. One of the side effects of bisphosphonates is damage to the esophagus; including esophagitis, esophageal erosions and esophageal ulcers. Other common side effects include inflammation of the eyes, musculoskeletal pains, and jaw necrosis. Common side effects of such drugs are described in detail in *Physicians' Desk Reference.* 62nd ed. Thomson Healthcare, 2008.

Enhancing bone anabolic functions (bone growth) by increasing the commitment of MSCs to the osteogenic lineage, and thereby increasing osteogenesis represents a promising new therapeutic strategy for osteoporosis and other diseases and conditions of the bone, such as those described supra. However, at present, little is known about the mechanisms and factors that govern MSC commitment to the osteogenic lineage, and even less is known about how to identify these important factors. Therefore, what is critically needed in the art are methods for identifying new agents or factors that can be used to enhance bone anabolic functions and treat conditions and diseases of the bone. The present invention provides such methods.

SUMMARY OF THE INVENTION

This invention relates to in vitro methods for identifying bone anabolic agents. The methods have been developed based on the present discovery that the transcription factor Sox2 plays an essential role in the self-renewal, proliferation and survival of cells of the osteoblastic lineage and may direct undifferentiated mesenchymal stem cells (MSCs) to the osteoblastic lineage. Therefore compounds that mimic Sox2 function or activate its expression in cells of the osteoblastic lineage are beneficial to osteoblastic expansion and may be used to treat osteoporosis or other bone degenerative disorders.

In one aspect, the present invention is directed to methods for identifying factors and pathways that play a role in and promote osteogenic commitment of MSCs for optimal bone repair. In another aspect, the present invention is directed to methods for identifying factors and pathways that promote proliferation of osteoblasts for bone growth and/or repair. In a further aspect, the present invention is useful for identifying new therapeutic targets for treatments for osteoporosis and other bone degenerative disorders characterized by osteopenia.

In another aspect, the present invention provides a method for identifying a compound capable of inducing bone growth, wherein the method involves the steps of: providing a Sox2 deficient cell having a Sox2 defect; contacting the Sox2 deficient cell with the compound; and determining if the compound rescued the Sox2 defect following the contacting step. In this aspect, the compound is determined to be useful for inducing bone growth if it rescued the Sox 2 defect.

In yet another aspect, the present invention provides a method for identifying a compound capable of inducing bone growth, wherein the method includes the steps of: quantifying at least one Sox2 responsive gene expression level in a wild-type cell; providing a Sox2 deficient cell having a Sox2 defect; contacting the Sox2 deficient cell with the compound; quantifying the gene expression level of at least one Sox2 responsive gene in the Sox2 deficient cell following the contacting step; and comparing the gene expression level of the Sox2 deficient cell to the gene expression level obtained from a wild-type cell. In this aspect, the compound is capable of inducing bone growth if the gene expression level of the Sox2 deficient cell is substantially similar to the gene expression level of the wild-type cell.

In certain aspects, the Sox2 deficient cell of the invention may be an osteoblast or a mesenchymal stem cell (MSC).

In other aspects of the invention, the Sox2 defect is characterized by an inability of the Sox2 deficient cell to proliferate, survive in culture, self-renew, or differentiate into an osteoblast.

In a further aspect, the gene expression level of a Sox2 responsive gene is determined by polymerase chain reaction (PCR).

These and other aspects of the present invention will be apparent to those of ordinary skill in the art in light of the present specification, claims and drawings.

BRIEF DESCRIPTION OF THE DRAWINGS

FIG. 4A: Western blot of GFP (black boxes) or CRE (white boxes) virus-infected osteoblasts: The Western blot shows knockout of Sox2 protein 72 hours after CRE infection in clones of $Sox2^{flox/flox}$ (F/F) or $Sox2^{flox/-}$ (F/-) but not in wild type (WT) cells.

FIG. 4B: Colony Assay: A graph of the results of the colony assay is shown. Percent (%) of colonies obtained in CRE infection are plotted as a percentage of the colonies in the corresponding GFP infection (100%) in five independent $Sox2^{flox/-}$ clones (F/-1-5) and one $Sox2^{flox/flox}$ clone (F/F(2)).

FIG. 4C: Fluorescent Microscopy: The colonies were examined under a fluorescence microscope (10× magnification) 6-10 days after infection with GFP or GFP-CRE retrovirus. Large, non-replicating cells are visible after Sox2 excision ($Sox^{flox/-}$).

As seen in the Example 5.

Figure 1:
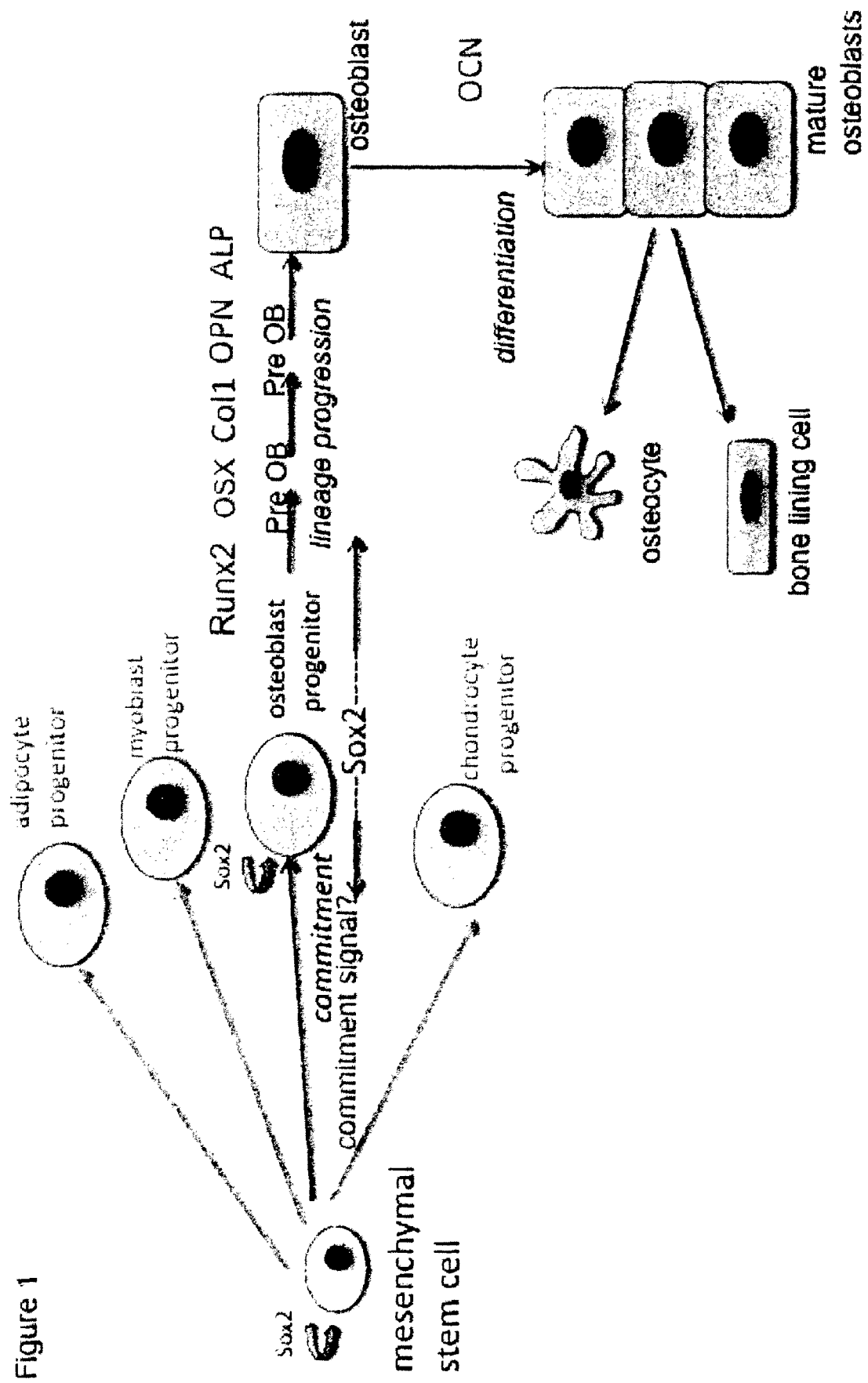
FIG. 1: Schematic of the osteoblast lineage: The stages of the osteoblastic lineage progression are shown. Markers of the osteoblast lineage are Runx2, osterix (osx), collagen1 (col1), osteopontin (OPN), alkaline phosphatase (ALP), and osteocalcin (OCN). The term "preOB" denotes "preosteoblastic" stages. The proposed role for Sox2 at different stages of the progression are illustrated.

Cell counts performed in parallel wells showed that this 5-6 fold difference in GFP and CRE infected cells is also reflected in cell number counts at 96 hours (our unpublished data). Thus the assay has an excellent range to enable identification of varying degrees of rescue.

The approximate analysis time for the plate reader for each plate is approximately 30 seconds. Data obtained from the primary screen will be analyzed using HTS-Corrector Software (28). Fluorescence readout from each well will be normalized by converting to a z score. The raw mean and standard deviation (S.D.) will be calculated from all test wells of a single plate. All data points that are more than three S.D.s away from the raw mean are excluded. The corrected mean ($x_c$) and the S.D.(s) of the filtered data will be calculated. The final z score for each plate for the assay will be calculated using the formula $z=(x_i-x_c)/s$, where $x_i$ is the raw measurement for the ith compound in the plate. Based on our assessments, compounds with a z-score of >+1.5 and <−1.5 will be designated as hits (29). Any compound that shows a positive z-score of greater than 1.5 will be considered to be a potential "hit". DMSO and SB431542 will serve as negative and positive control controls respectively and will be employed in all statistical analysis. This protocol routinely yields a Z' factor of 0.7.

Secondary reporter-based screen (under development)-: The purpose of the secondary screen is to further validate targets from the primary screen. We have previously published that the Connective Tissue Growth Factor (CTGF) gene is a target of FGF and is suppressed in osteoblasts in which Sox2 is over expressed (8, and our unpublished observation). Conversely, levels of CTGF are dramatically up-regulated following the deletion of Sox2 in osteoblasts (our unpublished results). Thus, CTGF levels are inversely related to Sox2 expression and can serve as a sensitive read-out for Sox2 levels. We will establish a stable osteoblast cell line derived from the F/- cell line to express a Firefly luciferase construct (pGL3-basic vector) under the control of the CTGF promoter (PCR cloning) Additionally, the cell line will also expresses the Renilla luciferase gene under the control of the thymidine kinase promoter. The Renilla luciferase gene serves as a negative control. Similar to the setup described in the previous section, GFP-control and Cre-virus infected F/- osteoblasts expressing the Firefly-CTGF and the Renilla control vectors will be plated at a density of $2.5\times10^3$ cells/well in a flat-bottomed, white 96-well plate (Corning, N.Y.). The next day, either DMSO or different concentrations of SB431542 (2, 5 and 10 µM) will be added. Luciferase activity will be read after 24, 48 and 72 hours after drug treatment. Fifteen microliters of Dual-Glo (Promega, Wis.) will be added to each well and incubated at room temperature for 15 minutes and Luciferase units will be measured. Following this measurement, 15 µl of Stop-and-Glo reagent (Promega, Wis.) will be added to each well, incubated at room temperature for 15 minutes and Renilla activity will be measured using the Perkin-ElmerTriLux reader. After estimating the Firefly/Renilla ratio, the raw mean and standard deviation (S.D.) will be calculated from all test wells of a single plate. All data points that are more than three S.D.s away from the raw mean are excluded. The corrected mean ($x_c$) and the S.D.(s) of the filtered data will be calculated. The final z score for each plate for the assay will be calculated using the formula $z=(x_i-x_c)/s$, where $x_i$ is the raw measurement for the ith compound in the plate. Based on our preliminary screens, compounds with a z-score of >+1.5 and <−1.5 will be designated as confirmed hits. Any compound that shows a positive z-score of greater than 1.5 will be considered to be a confirmed "hit". As previously mentioned in the Preliminary data section, DMSO and SB431542 (Sigma, St Louis, Mo.) will serve as negative and positive control controls respectively and will be employed in all statistical analysis.

Luciferase units are expected to increase in CRE-infected cells and decreased in the presence of positive hits (identified from primary screen) that mimic Sox2.

In addition to a secondary screen, a stringent "tertiary" counter screen is used. In this screen, akin to the colony-forming assay described in FIG. 4B and BasuRoy et al (31). GFP and CRE-lentivirus infected F/- osteoblasts will be plated in clear, flat-bottomed 96-well plates (Corning, N.Y.) at a density of 50 cells/well in 10 µM of a test compound and incubated for 48 hours. Following the incubation period, the cells will be fixed in 4% paraformaldehyde and imaged using the Molecular Devices Discovery1/Image Express (WCMC). This tertiary screen eliminates false positives obtained in the secondary screen.

CONCLUSION

This application is based on our very recent and novel finding that the transcription factor Sox2 is required for the self-renewal/survival of osteoblasts (31).

The assays described will be used for high throughput screening to identify compounds that can be tested in murine models of osteoporosis to determine their ability to prevent bone loss. Compounds that can mimic the function of a survival factor of the osteoblast lineage represent a unique opportunity for drug discovery and development of new bone anabolics.

Findings presented herein have led to the discovery that Sox2 is a key regulator early in the osteoblast lineage and we are presently studying the mechanism by which Sox2 regulates osteoblast survival. In line with this discovery, a recent report demonstrates that transgenic Sox2 expression can expand the pool of undifferentiated MSCs in bone marrow (4,). Several groups have reported an anabolic effect of FGF treatment in vivo in bone formation, a finding that still awaits a mechanistic explanation (5,6). However, FGF has widespread effects and is unlikely to be a safe bone anabolic. MSCs persist in adult organisms and contribute to the replacement of osteoblasts in bone turnover and fracture healing. The bone anabolic effect of FGF in vivo may result partly from its ability to induce Sox2 and expand the pool of MSCs or osteoprogenitors that commit to the osteoblastic lineage. Sox2 by itself is a nuclear transcription factor that would not be easy to get into cells but small molecules that mimic or induce Sox2 would be expected to easily enter cells. Such Sox2 mimetics have been identified using small molecule libraries in fibroblasts that are induced to form pluripotent stem cells (7, 32). The unique cell-based system disclosed herein can harness the function of Sox2 in osteoblasts to identify agents that promote osteoblast survival and function. This system can be readily optimized to meet the requirements of HTS for small molecule mimetics of Sox2. Additionally, the system is unique in that the primary and secondary screens can be performed in the same cell lines thus minimizing systematic errors.

Significance and potential applicability: Despite years of cell culture studies on osteoblast biology, our knowledge about the origins, fate and life span of cells along this lineage is limited, and only a few markers are known for staging osteoblasts. The most extensively studied primary osteoblast cultures are derived from calvaria (skull) or by differentiation of bone marrow-derived mesenchymal stem cells (MSCs). MSCs from bone marrow have the capacity to differentiate into cells of the connective tissue lineage including bone, fat, cartilage and muscle. Calvarial osteoblasts are derived from the differentiation of mesenchymal cells which have also been reported to be multipotent as they also have the potential to enter the chondrogenic (cartilage) and adipogenic (fat) lineages. Cultured embryonic and newborn murine calvarial cells are usually a mixed population of MSCs, osteoprogenitors and osteoblasts, and the relative amounts of these different populations depend on the age of the calvaria and the culture conditions. However, the signals that regulate the potency, expansion, and commitment of mesenchymal cells to the osteoblast lineage remain to be defined.

The Sox2 based assay claimed herein is designed to identify compounds that can "mimic" the effect of Sox2 and rescue lethality caused by Sox2 depletion in osteoblasts. Compounds identified in the high throughput may eventually also have uses in other diseases of the bone such as healing of fractures, and arthritis since several of these patho-physiological conditions rely on bone repair by MSCs. Finally, our screen might also help identify new players in the MSC differentiation pathway. The high affinity mimetics that we identify maybe used for the biochemical purification and characterization of the MSC differentiation pathway.

DETAILED DESCRIPTION OF THE INVENTION

The present invention is directed to methods for identifying bone anabolic agents. As used herein, bone anabolic agents are defined as factors, such as, but not limited to, cytokines, transcription factors or other small molecules that are useful for increasing bone growth. In some embodiments, the methods of the present invention are directed to identifying factors that induce osteoblast proliferation. The ability to induce osteoblast proliferation is important for treating conditions characterized by loss of bone density.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

The term "agent" as used herein refers to compounds, chemicals, small molecules, or other factors that are useful for inducing bone growth, as determined by the methods of the present invention.

In certain aspects, the methods of the invention are directed to identifying factors that drive mesenchymal stem cells (MSCs) to proliferate and differentiate into cells of the osteoblast lineage. Modulation of stem cell differentiation in the adult mammal represents an important area of research, as the ability to control stem cell differentiation into cells of specific desired lineage can lead to the regeneration of tissue for the treatment of disease, conditions and injury.

Stem cells are capable of producing either new stem cells (self-renewal) or cells called progenitor cells that differentiate to produce the specialized cells found in mammalian organs. Symmetric division occurs where one stem cell divides into two daughter stem cells. Asymmetric division occurs where one stem cell forms one new stem cell and one progenitor cell. A progenitor cell differentiates to produce the mature specialized cells of mammalian organs. In contrast, stem cells never terminally differentiate (i.e., they never differentiate into a specialized tissue cell). In the present invention, MSCs are induced to differentiate into osteoprogenitor cells, or bone progenitor cells. The transcription factor Sox2 is critically involved in this process.

Cells of the osteoblast lineage are responsible for synthesis, deposition and mineralization of matrix in bone formation. Despite years of cell culture studies on osteoblast biology, knowledge in the art about the origins, fate and life span of cells along the osteoblast lineage is limited, and only a few markers are known for staging osteoblasts. Primitive osteoprogenitors arise from multipotent MSCs that commit to the osteoblast lineage and differentiate to preosteoblasts and mature osteoblasts.

The earliest known marker and regulator for the osteoblast lineage is the transcription factor Runx2/Cbfa1. Another crucial regulator of osteoblastogenesis downstream of Runx2 is the transcription factor, osterix (OSX). As preosteoblasts expressing Runx2 and OSX differentiate further along the osteoblast lineage, they gradually stop proliferating, as they synthesize and deposit matrix proteins, notably Collagen1 (col1). Differentiation then proceeds to mature osteoblasts along with the expression of osteocalcin (OCN). Finally the matrix is mineralized to generate bone. This lineage progression from MSC to mature osteoblast and bone in shown in FIG. 1.

The signals that regulate the potency, expansion, and commitment of MSCs to the osteoblast lineage remain to be defined. In the present invention, it has been discovered that expression of the transcription factor Sox2 is required for the self-renewal and maintenance of osteoblast/osteoprogenitor cells in vitro, and that its inactivation leads to a dramatic cessation of growth of these cultures. Sox2 plays a well-known role in embryonic stem (ES) cells and is also involved in reprogramming somatic cells to pluripotent cells (induced pluripotent cells), where it is required to maintain self-renewal and pluripotency (2, 33). The involvement of Sox2 in MSC self renewal and maintenance is illustrated in FIG. 1.

The nucleic acid and amino acid sequences of human and murine Sox2 are known and have been described (9). The human nucleic acid sequence has GenBank® Accession No. [NG_009080] (SEQ ID NO: 1) and the murine nucleic acid sequence has GenBank® Accession No. U31967 (SEQ ID NO: 2). The human amino acid sequence has GenBank® Accession No. P48431-1 (SEQ ID NO: 3) and the murine amino acid sequence has GenBank® Accession No. AAC31791 (SEQ ID NO: 4).

Sox2 expression was originally thought to be restricted to uncommitted stem cells and to the adult central nervous system (CNS). However, more recent reports clearly demonstrate that Sox2 expression persists in many adult tissues where its precise role is less well-defined. Sox2 is expressed by calvarial osteoblasts and is induced by fibroblast growth factor (FGF) (1). Similar to FGF treatment, high levels of ectopically expressed Sox2 can prevent differentiation of osteoblasts in culture (1,3). A recent report also demonstrates that transgenic Sox2 expression can expand the pool of undifferentiated MSCs in bone marrow (4). Several groups have reported an anabolic effect of FGF treatment in vivo in bone formation, a finding that still awaits a mechanistic explanation (5,6). MSCs persist in adult organisms and contribute to the replacement of osteoblasts in bone turnover and fracture healing. This suggests that the bone anabolic effect of FGF in vivo may result from its ability to induce Sox2 and expand the pool of MSCs that commit to the osteoblastic lineage.

Studies of the FGF response of osteoblasts, that alone are responsible for the formation of the flat bones of the skull, have shown that FGF treatment stimulates cell proliferation and inhibits differentiation (3). Osteoblast gene expression studies showed that FGF signaling antagonizes the Wnt pathway, that is known to promote differentiation. One of the mechanisms through which FGF antagonizes Wnt signaling is by inducing the expression of the transcription factor, Sox2, which can associate with β-catenin, a key effector of Wnt signaling, and inhibit its activity (1,8).

Figure 2:
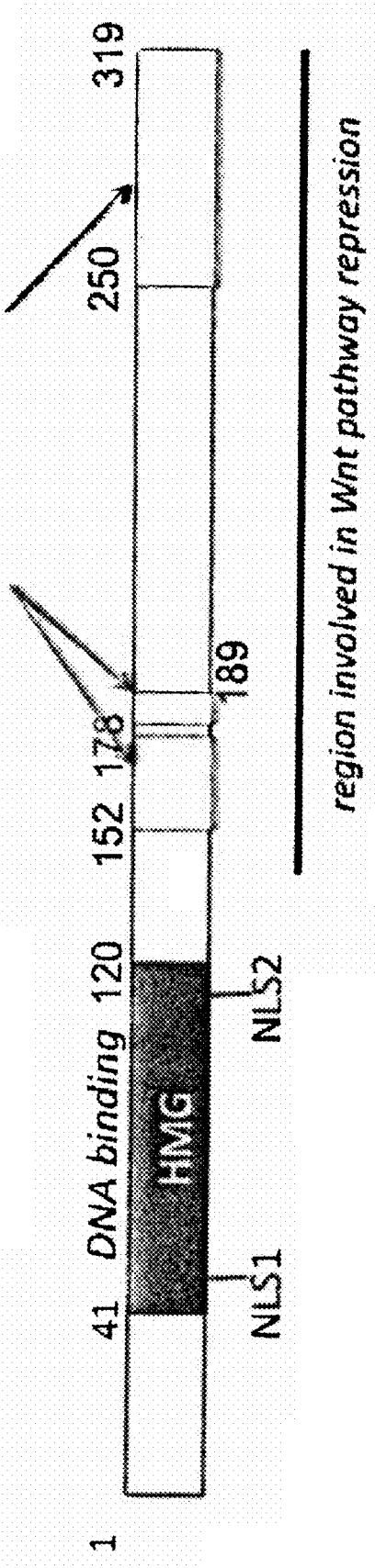
FIG. 2: Schematic of Sox2 protein: The HMG-DNA binding domain begins at residue 41 (left-most rectangle) and contains two nuclear localization signals (NLS1 and NLS2). The three transactivation domains (arrows) have transactivation activity with Oct-4 on the FGF-4 enhancer. The C-terminal portion that is capable of repressing a Wnt-responsive reporter when a nuclear localization signal is provided.

Sox2 (see, FIG. 2) is a member of the HMG Domain, SRY-related Sox family of transcription factors, that has been shown to be an important transcriptional activator in ES cells and master regulator of ES cell maintenance, and to have an essential role in the development of the CNS, eye and gut. Several mutant forms of Sox2 have been described, which can be introduced into ES cells to "rescue" the effects of Sox2 deletion (1, 8-11). Furthermore, Sox2 has been recently shown to play a critical role in the reprogramming of iPS cells (2).

Like other Sox factors, Sox2 binds DNA in the minor groove at the consensus sequence T/AT/ACAAAGA and causes strong DNA bending. Sox2 was originally identified, together with Oct-4, as an essential factor in the transcription of the FGF4 gene in ES and EC cells (9). Sox2 and Oct-4 bind cooperatively to the FGF4 enhancer DNA through their DNA binding, HMG and POU domains, respectively and synergistically activate transcription. Cooperative binding of these factors to the enhancer DNA tethers each factor to DNA and increases the activity of intrinsic and latent activation domains within each protein (10, 11). The same synergy was found to operate in the transactivation by Sox2 and Oct-4 of other ES cells target genes, such as UTF-1, Nanog, and Oct-4 and Sox2 themselves.

Sox2 may also have other functions beyond that of a direct transcriptional regulator. Sox2 can associate with β-catenin and inhibit its ability to promote transcription (1,12). This function is conserved in other members of the Sox family (e.g., Sox9), maps to the C-terminal domain of Sox2 and does not require the DNA binding domain. Thus, it cannot be excluded that some of the effects of Sox2 expression may depend on its ability to bind and regulate the activity of additional proteins. Therefore, the role of Sox2 in osteoblast survival may also depend on its interaction with other proteins that may regulate signaling pathways or regulate gene expression.

As used herein the term "Sox2 gene target" is a gene that has an expression which is regulated directly or indirectly by the action of Sox2 (e.g., by the transcriptional activity of Sox2). In other words, a Sox2 gene target's expression may be activated or repressed by the action of Sox2.

In the present invention, in order to test the role of Sox2 in osteoblast development in vivo, conditional knockout (CKO) mice are generated. An approach using CKO mice allows for the specific deletion of a single target gene in a specific cell type, through the use of a cell-specific promoter. The most commonly used technique for conditional gene knockout is the Cre-loxP recombinase system. Cre recombinase (Cre), is a Type I topoisomerase from P1 bacteriophage that catalyzes site-specific recombination of DNA between loxP sites. The enzyme does not require any energy cofactors and Cre-mediated recombination quickly reaches equilibrium between substrate and reaction products. The loxP recognition element is a 34 base pair (bp) sequence comprised of two 13 bp inverted repeats flanking an 8 bp spacer region which confers directionality. Recombination products are dependent on the location and relative orientation of the loxP sites. Two DNA species containing single loxP sites will be fused while DNA between loxP sites in the same orientation will be excised in circular form and DNA between opposing loxP sites will be inverted with respect to the rest of the DNA.

Cre recombinase is used as a tool to modify genes and chromosomes. In this approach the Cre recombinase is used to delete a segment of DNA flanked by LoxP sites ("floxed") in an experimental animal. It has been used to generate animals with mutations limited to certain cell types (tissue-specific knockout) or animals with mutations that can be activated by drug administration (inducible knockout) in a number of transgenic species. See, Akagi K, Sandig V, Vooijs M, Van der Valk M, Giovannini M, Strauss M, Berns A (1997). Cre-mediated somatic site-specific recombination in mice. Nucleic Acids Res. 25 (9): 1766-73. The availability of transgenic lines with tissue specific or inducible Cre expression permits researchers to inactivate or activate a gene of interest simply by breeding a foxed animal to pre-existing Cre-transgenics.

For example, in the present invention, mice are generated having a Sox2$^{flox/geo}$ phenotype. Specifically, one Sox2 allele is "floxed" (bracketed by loxP sequences), which provides a target for the Cre recombinase, as described, supra. The other Sox2 allele is replaced by the β-galactosidase (geo) reporter gene, which is well known in the art for use as a reporter gene. Briefly, when β-galactosidase is expressed, the breakdown of its substrate can be rapidly and easily detected using commercially available reagents. This creates a Sox2$^{flox/null(-)}$ mouse that is phenotypically normal (i.e., appears to have no physiological differences compared to a wild-type mouse), having a single, floxed allele of Sox2.

To create the Sox2 CKO mouse, the Sox2$^{flox/-}$ mouse is crossed with transgenic mice expressing the Cre recombinase under the control of the 2.3 kb collagen I promoter, which is specifically expressed in the osteoblastic lineage (22). F1 offspring are intercrossed and F2 offspring are screened for the presence of both the Sox2$^{flox/-}$ phenotype and the Cre recombinase gene. Since the Sox2 CKO mice carrying the Cre gene are mostly sterile, they can only be obtained as F2 progeny from heterozygous crosses. In the selected mice, Cre recombinase is expressed in osteoblasts, leading to the excision of the fluxed Sox2 gene (22). The primers used in PCR reactions for screening the CKO mice are listed in Table 1, below:

TABLE 1

Primer Sequences for Conditional Knockout Mouse Screening

| SEQ ID NO: | Primer Name | Sequence |
| --- | --- | --- |
| 5 | del flox forward | GAC CTA GCC AGA CCC CCT TA |
| 6 | 47 alternate reverse | AGA TAA GTG GGA GGT TAA GCG AGG |
| 7 | del flox reverse | CGT TGG CTA CCC GTG ATA TT |
| 8 | Flox forward | GTG AGA CGT GCT ACT TCC ATT TGT C |
| 9 | Flox reverse | AGG CTG AGT CGG GTC AAT TA |

Polymerase chain reaction (PCR) is a well-known method that allows exponential amplification of short DNA sequences (usually 100 to 600 bases) within a longer double stranded DNA molecule. PCR entails the use of a pair of primers, each about 20 nucleotides in length, that are complementary to a defined sequence on each of the two strands of the DNA. These primers are extended by a DNA polymerase so that a copy is made of the designated sequence. After making this copy, the same primers can be used again, not only to make another copy of the input DNA strand but also of the short copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is analyzed on an agarose gel and is abundant enough to be detected with an ethidium bromide stain.

In other embodiments, real-time PCR, also called quantitative real time PCR, quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample. For example, in the embodiments disclosed herein, qPCR may be used to quantify the amount of fungal DNA in a patient sample. The procedure follows the general principle of PCR; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce upon binding to complementary DNA (such as with molecular beacons) or with completion of each PCR cycle (such as with dual labeled probes rendered more fluorescent with the 5' exonuclease activity of polymerase enzymes).

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., (1991) Gene 108:1), *E. coli* DNA polymerase I (Lecomte and Doubleday (1983) Nucleic Acids Res. 11:7505), T7 DNA polymerase (Nordstrom et al. (1981) J. Biol. Chem. 256: 3112), *Thermus thermophilus* (Tth) DNA polymerase (Myers and Gelfand (1991) Biochemistry 30:7661), *Bacillus stearothermophilus* DNA polymerase (Stenesh and McGowan (1977) Biochim Biophys Acta 475:32), *Thermococcus litoralis* (Tli) DNA polymerase (also referred to as Vent DNA polymerase, Cariello et al. (1991) Nucleic Acids Res 19:4193), *Thermotoga maritima* (Tma) DNA polymerase (Diaz and Sabino (1998) Braz J. Med. Res 31:1239), *Thermus aquaticus* (Taq) DNA polymerase (Chien et al., (1976) J. Bacteoriol 127:1550), *Pyrococcus kodakaraensis* KOD DNA polymerase (Takagi et al. (1997) Appl. Environ. Microbiol. 63:4504), JDF-3 DNA polymerase (Patent application WO 0132887), and *Pyrococcus* GB-D (PGB-D) DNA polymerase (Juncosa-Ginesta et al. (1994) Biotechniques 16:820). The polymerase activity of any of the above enzymes can be determined by means well known in the art.

In certain embodiments of the invention, the expression of Sox2 in bone marrow-derived MSCs (BM-MSCs) is determined. It has been reported that MSCs express Sox2 (27), and Sox2 mRNA is detectable at significant levels in undifferentiated murine MSCs. In certain embodiments, Sox2 gene expression in MSCs is determined as the MSCs are induced to differentiate into the osteoblastic or adipocyte lineage. As cells are induced to differentiate into these lineages, the expression of Sox2, as well as differentiation markers characteristic of each lineage, are measured at time intervals.

In certain embodiments, BM-MSC derived from Sox2$^{flox/-}$; Cre mice are used to study the role of Sox2 in MSC self-renewal and/or differentiation. In some embodiments, it is determined whether proliferation in culture favors Sox2 positive cells, and whether osteogenic differentiation depends on the expression of the Sox2 gene. In certain embodiments, the cultured MSC from the Sox2$^{flox/-}$; Cre mice are infected with the Cre-virus to inactivate Sox2 in culture.

As shown in the Examples below, the present discovery that expression of Sox2 is required for the self-renewal and maintenance of osteoblast/osteoprogenitor cells in vitro, and that its inactivation leads to a dramatic cessation of growth of these cultures, is further highlighted by the additional discovery that genetically altered mice having reduced levels of Sox2 in osteoblasts have low bone density (i.e., are osteopenic). Specifically, the calvaria of osteopenic mice with a Cre-mediated, conditional knockout (CKO) of the Sox2 gene in the osteoblastic lineage, show a high degree of mosaicism, such that the majority of the cells still contain an active Sox2 gene. The term "mosaicism" denotes the presence of two populations of cells with different genotypes in one individual.

Furthermore, culturing calvarial osteoblasts from these mutant mice produces only cells expressing Sox2, and cells with the Sox2 null genotype can not be propagated in culture. Excision of the Sox2 gene in cultures of osteoblasts carrying floxed "alleles" of Sox2 by infection with a Cre-expressing retrovirus causes extensive inhibition of proliferation and, again, viable Sox2 null cells cannot be isolated (31). These and other results strongly suggest that Sox2 expression is required for self-renewal of osteoblast/osteoprogenitor cells and that Sox2 inactivation causes exhaustion of proliferative ability and/or terminal differentiation.

As used herein, the term "Sox2 null" is interchangeable with the term "Sox2 deficient." These terms are defined to mean that the Sox2 gene and/or protein is non-functioning, has decreased or impaired function, or is absent (i.e., deleted or degraded). Herein, the term "Sox2 defect" is meant to encompass any condition of a cell or organism that results in an impaired or abolished function of the Sox2 gene or protein. Such a Sox2 defect may occur at the transcriptional, translational, or post-translational level.

Immortalized Cells

In certain embodiments, immortalized cells are generated. Immortalized cells may be made, for example, by infecting primary osteoblasts with a retrovirus, such as pBabe-puro, expressing PyLT. PyLT plays a key role in regulating the viral life cycle by binding to the viral origin of DNA replication where it promotes DNA synthesis. PyLT modulates cellular signaling pathways in the host to stimulate progression of the cell cycle into S-phase, thereby promoting viral replication, by binding to a number of cellular control proteins. This is achieved by inactivation of the Rb proteins, but not p53, and stimulating cell growth pathways by binding cellular DNA, ATPase-helicase, DNA polymerase a association, and binding of transcription preinitiation complex factors. Detection of PyLT may be determined in immortalized cells using a commercially-available detecting antibody specific for PyLT. In other embodiments, cells may also be immortalized by expression of SV-40 large T antigen, c-myc, telomerase or spontaneously by serial passaging.

Retroviruses

In the present invention, retroviruses are used. A non-limiting example of the retroviruses contemplated for use in the present invention is pbabe, e.g., pBabe-puro, available from Addgene, Inc. (Cambridge, Mass.). Suitable systems are described, for example, in Current Protocols in Molecular Biology, F. Ausubel et al., Ed., Wiley Interscience, New York 1997.

In certain embodiments of the invention, genetic rescue experiments are performed to assess the ability of wild type Sox2 to rescue the cell lethality induced by excision of the Sox2 gene. This type of experiment "adds back" the gene that is deleted in order to determine if certain functions of the cell are restored (e.g., ability to survive, self-renew, and/or proliferate) by restoration of the deleted gene. A "transgenic" copy of wild type or mutant forms of Sox2 can be introduced using lentivirus vectors to deliver the gene into immortalized Sox2$^{flox/-}$ osteoblasts in vitro.

In general, the term "rescue" is defined herein to mean that a Sox2 defect is overcome. For example, a Sox2 deficient cell, which is unable to survive, proliferate, and/or differentiate in culture, is "rescued", if upon treatment, e.g., with a screening compound, the Sox2 deficient cell becomes able to survive, proliferate, and/or differentiate in culture. In some embodiments, rescue of a Sox2 defect will restore the phenotype of a Sox2 deficient cell to one which is similar to the phenotype of a wild-type cell. As used herein, the term "wild-type cell" is defined as a cell that is not Sox2 deficient (i.e., that does not have a Sox2 defect).

In other embodiments of the invention, a transgenic copy of one or more mutant Sox2 genes may also be introduced into immortalized Sox2$^{flox/-}$ osteoblasts in vitro. The use of mutant Sox2 "rescue" experiments allows for the determination of whether the requirement for the specific domains of Sox2 that are involved in its canonical activity of a transcriptional regulator (DNA binding, nuclear localization, presence of trans-activation domains) are also operative in this situation. Mutants of Sox2 have been described previously (10).

Lentiviruses

In the present invention, Lentiviruses are used. Lentiviruses are a subclass of Retroviruses. They have recently been adapted as gene delivery vehicles (vectors) due to their ability to integrate into the genome of non-dividing cells. This is a unique feature of Lentiviruses, as Retroviruses can infect only dividing cells. The viral genome in the form of RNA is reverse-transcribed when the virus enters the cell to produce DNA, which is then inserted into the genome at a random position, by the viral integrase enzyme. The vector, now called a provirus, remains in the genome and is passed on to the progeny of the cell when it divides.

For safety reasons, Lentiviral vectors never carry the genes required for their replication. To produce a Lentivirus vector, several plasmids are transfected into a so-called packaging cell line, commonly 293FT cells (commercially available from Invitrogen). One or more plasmids, generally referred to as packaging plasmids, encode the virion proteins, such as the capsid and the reverse transcriptase. Another plasmid contains the genetic material to be delivered by the vector. It is transcribed to produce the single-stranded RNA viral genome and is marked by the presence of the ¤ (psi) sequence. This sequence is used to package the genome into the virion. (Invitrogen).

Lentivirus vectors that may be used in the present invention include but are not limited to cFUCRW, cFUW, and H163, available from Addgene, Inc. (Cambridge, Mass.).

Screening Assay:

The present invention provides methods for screening bone anabolic agents. In certain embodiments, the screening assay is performed on Sox2 null primary or immortalized osteoblasts in vitro. Examples of methods for making Sox2 null osteoblasts include transduction of Sox2$^{flox/-}$ cells with a retrovirus carrying CRE recombinase, as described supra. However other methods known in the art may be used to achieve the Sox2 null phenotype, such as, but not limited to gene knockdown using RNAi (interfering RNA, such as, e.g., siRNA).

In certain embodiments, the screening assay detects compounds or agents which "rescue" the Sox2 null phenotype of the cultured osteoblasts. As discussed, supra, for example, such agents or compounds, when co-introduced into Sox2$^{flox/-}$ osteoblasts with the CRE recombinase retrovirus (or, e.g., with siRNA to knock down Sox2 in wild type osteoblasts) are screened to determine whether they rescue the Sox2 null phenotype (i.e., failure to survive, proliferate and/or differentiate).

In other embodiments, in order to determine whether the screening agents rescue the Sox2 null phenotype, the expression of Sox2 responsive genes may be detected and used as a read-out for the bone anabolic function of a screening compound. In certain embodiments, Sox2 responsive genes are identified by microarray analysis and may be used in a screening assay. Specifically, since Sox2 is a transcription factor, it is expected that its function in promoting osteoblast self-renewal and expansion depends on its ability to regulate the expression of specific gene(s). These Sox2 gene targets may be identified, and then compounds that directly activate or repress the expression or function of these genes may be identified by an assay that utilizes cells in which the gene or genes can be inactivated.

Microarray Analysis:

Sox2 activity as a transcriptional regulator in maintaining osteoblast self-renewal affects gene expression. Changes in gene expression following the introduction of the Cre recombinase into Sox2$^{flox/-}$ cells and Sox2 excision may be monitored, for example, using Affymetrix® mouse gene expression arrays. RNA is extracted from the Sox2 null cells at predetermined time points, processed into cDNA and cRNA and hybridized as previously described (1, 8, 14).

The screening assay is useful for identifying bone anabolic agents to promote bone formation. The identified agents may be used in pharmaceutical compositions and formulations. For example, small molecules identified using the screening assay may be used in therapeutic treatments of bone diseases or conditions characterized by osteopenia, such as, but not limited to osteoporosis. Osteopenia is a condition where bone mineral density (BMD) is lower than normal. BMD is a medical term referring to the amount of matter per cubic centimeter of bones. It is measured by a procedure called densitometry, often performed in the radiology or nuclear medicine departments of hospitals or clinics. The measurement is painless and non-invasive and involves minimal radiation exposure. Measurements are most commonly made over the lumbar spine and over the upper part of the hip. The forearm may also be scanned if either the hip or the lumbar spine cannot be.

Osteopenia is considered by many doctors to be a precursor to osteoporosis. However, not every person diagnosed with osteopenia will develop osteoporosis. Osteopenia is defined as a bone mineral density T score between −1.0 and −2.5. The T-score is a comparison of a patient's BMD to that of a healthy thirty-year-old of the same sex and ethnicity. This value is used in post-menopausal women and men over age 50 because it better predicts risk of future fracture. The criteria of the World Health Organization are: Normal is a T-score of −1.0 or higher; osteopenia is defined as less than −1.0 and greater than −2.5; and osteoporosis is defined as −2.5 or lower, meaning a bone density that is two and a half standard deviations below the mean of a thirty year old woman. See, WHO (1994). "Assessment of fracture risk and its application to screening for postmenopausal osteoporosis. Report of a WHO Study Group". World Health Organization technical report series 843: 1-129.

Like osteoporosis, osteopenia occurs more frequently in post-menopausal women compared to pre-menopausal women as a result of the loss of estrogen. It can also be exacerbated by lifestyle factors such as lack of exercise, excess consumption of alcohol, smoking or prolonged use of glucocorticoid medications such as those prescribed for asthma. Other examples of such conditions include patients undergoing treatment for inflammatory bowel disease, who often suffer from decreased bone density, and would benefit from new therapeutic bone anabolic agents identified by the methods according to the present invention.

The osteopenia condition can occur in young women who are athletes. It is associated with female athlete triad syndrome as one of the three components, the other two being amenorrhea and disordered eating. Female athletes tend to have lower body weight, lower fat percentage, and higher incidence of asthma than their less active peers. The low estrogen levels (stored in body fat) and/or use of corticosteroids to treat asthma or autoimmune diseases can significantly weaken bone over long periods of time. Distance runners in particular are also discouraged from consuming milk products when training, which would result in lower calcium absorption than other groups. It is also a sign of normal aging, in contrast to osteoporosis which is present in pathologic aging.

It is understood by those skilled in the art that mouse models and in vitro models, such as those described herein, are predictive of results and/or efficacy in humans.

In certain embodiments, bone anabolic agents identified by the methods of the present invention may be used in therapeutic treatments of osteoporosis or other diseases or conditions characterized by osteopenia. Contemplated by the present invention are pharmaceutical compositions and formulations comprising one or more anabolic agents identified by the methods of the present invention.

The term "therapeutically effective" when applied to a dose or an amount refers to that quantity of a compound or pharmaceutical composition that is sufficient to result in a desired activity upon administration to a mammal in need thereof. As used herein, the term "therapeutically effective amount/dose" refers to the amount/dose of a pharmaceutical composition containing a bone anabolic agent identified by any of the methods of the present invention that is suitable for treating a patient having a disease or condition characterized by osteopenia. In certain embodiments the patient may be a mammal. In other embodiments, the patient is a human.

The present invention also provides pharmaceutical formulations or dosage forms for administration to mammals in need thereof.

When formulated in a pharmaceutical composition, the bone anabolic agents identified by the methods of the present invention can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicles with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage from carrier, including but not limited to one or more of a binder (for compressed pills), an encapsulating agent, a flavorant, and a colorant. Suitable pharmaceutical carriers are described in "Remington's Pharmaceutical Sciences" by E. W. Martin.

EXAMPLES

The present invention is described further below in working examples which are intended to further describe the invention without limiting the scope therein.

In the examples below, the following materials and methods were used.

Reagents:

All reagents were purchased from Sigma-Aldrich, and were of the highest grade possible, St. Louis, Mich. Tissue culture supplies were obtained from Invitrogen, Carlsbad, Calif., and tissue culture plastic ware was purchased from Fisher-Scientific.

Generation of Sox2-Floxed Mice:

Sox2 CKO mice were obtained from Dr. Silvia Nicolis, University of Milan, Bicocca. They were made by homologous recombination of the Sox2 gene flanked by loxP sites, which enable the excision of Sox2 upon exposure to Cre recombinase.

TABLE 2

Primers used for genotyping Sox-2-flox mice:
Sox2 Screening Primers

| SEQ ID NO: | Primer Name | SEQUENCE | Tm (° C.) |
|---|---|---|---|
| 10 | 5' Sox2 (33) | GAC CTA GCC AGA CCC CCT TA | 61.4 |
| 11 | 5' Sox2 (47) | AGA TAA GTG GGA GGT TAA GCG AGG | 62.7 |
| 12 | neo 3' (56) | CGT TGG CTA CCC GTG ATA TT | 57.3 |
| 13 | pGKpr (46) | GTG AGA CGT GCT ACT TCC ATT TGT C | 63.0 |
| 14 | 3' Sox2 (24) | AGG CTG AGT CGG GTC AAT TA | 57.3 |

The primer pair combination 33/56 is called "del flox" and was used to detect the deleted Sox2 allele after Cre recombination. The primer pair combination 24/46 is called "flox" and was used to detect the deleted and undeleted flox alleles. The primer pair combination 24/56 is referred to as "beta geo" and was used to detect the deleted Sox2 allele replaced with the beta-galactosidase reporter gene. The 33/47 primer pair flanks the 5' loxP site and produces two bands in the floxed heterozygous configuration. The "Tm" shown above is the melting temperature of each primer.

Isolation and Culture of Mouse P1 Osteoblasts:

Calvaria from newborn mice were dissected free of surrounding muscles and soft tissues and washed in PBS containing penicillin and streptomycin. Isolated calvaria were sequentially digested in αMEM (GIBCO BRL), containing 0.1% collagenase and 0.2% dispase at 37° C. Digested fractions were collected every 10 min and fractions 2-5 were pooled. Cells were collected by centrifugation and resuspended in αMEM supplemented with 10% fetal calf serum (FCS). To study the differentiation of osteoblasts, cells were cultured for up to 21 days in growth media containing ascorbic acid (AA; 100 μg/ml) and β-glycerophosphate (BGP; 4 mM) and medium was changed every 3 day.

Immortalization of Primary Osteoblasts and Isolation of Osteoblast Clones:

Primary osteoblasts were infected with a retrovirus (pBabe-puro) expressing the Polyoma large T-Antigen. The cells were infected for 1 hour (h) in the presence of 8 μg/ml of polybrene. The virus stock was produced in 293 cells as described previously. Clones were selected using 4 μg/ml of puromycin for 2 weeks (wk). Immortalized clones OB1-4 were characterized according to morphology, histochemical staining for alkaline phosphatase and for their ability to express osteocalcin upon differentiation. Expression of Polyoma large T-Ag was determined by immunofluorescence using an anti-Polyoma large T-Ag rat serum. Pools of immortalized osteoblasts were then plated at limiting dilutions and single clones were isolated with cloning cylinders. Clones of the $Sox2^{F/F}$ and $Sox2^{F/-}$ were used for the study.

Isolation of Mouse Embryonic Fibroblasts (MEFS):

Mouse embryonic fibroblasts (MEFS) were isolated by the method described by Samuelson and Metzger in Cold Spring Harbor Protocols. Briefly, a 16-day pregnant female was euthanized by carbon dioxide asphyxiation. Embryos (E16.5) were retrieved and washed in sterile PBS containing penicillin and streptomycin. Embryos were decapitated and eviscerated using sterile dissection tools, and then digested in 0.1%

Trypsin-EDTA solution at 37° C. for 15 minutes. Digests were collected and neutralized with DMEM containing 10% FCS and plated in 6-cm dishes overnight. These were designated as p0 MEFs and were used for further experiments.

Detection of Deleted Sox2 Alleles in Cre-Infected Cells after Serial Passaging:

Sox2-floxed osteoblasts were infected with a retrovirus either encoding eGFP (MSCV-eGFP) or CRE (MSCV-CRE-eGFP) at a multiplicity of infection (MOI) of 10, in the presence of 8 µg/ml polybrene. Twenty-four (24) hours after infection, fresh medium was added to the plate and the cells were incubated for an additional 48 hours (72 hours total from the start of infection). The infected cells were then trypsinized and re-plated in a cluster-6 well plate. These cells were designated as passage 1 (p1). DNA was extracted from p1 cells, and p1 cells were also re-passaged (passage 2). Subsequent passaging and DNA extraction was carried out for a few passages until no green cells persisted in the Cre-infected cells (indicating lack of Cre expression). Presence of a deleted Sox2 allele in each passage (to detect efficient Cre-dependent excision) was verified using the PCR primers described above. Similar passaging experiments were also conducted with MEFs from Sox2 floxed E16.5 embryos.

Western Blot Analysis:

Cells were lysed in RIPA buffer (10 mM, Tris-HCl, pH 7.2, 150 mM NaCl, 5 mM EDTA, 0.1% SDS, 1% Na deoxycholate, 1% NP-40) containing protease inhibitor cocktail (from Roche, Nutley, N.J.) and phosphatase inhibitors (sodium orthovanadate). Protein concentration was determined using the Bio Rad (Hercules, Calif.) Bradford Protein Assay reagent. Equal amounts of protein were resolved on a 9% SDS-PAGE gel. Proteins were electrotransferred to nitrocellulose membrane and incubated with the specific antibodies. Proteins were visualized by ECL (Amersham Pharmacia Biotech, Piscataway, N.J.). Antibodies against Sox2 were purchased from Cell Signaling Technology (Danvers, Mass.). Other antibodies used included Cre antibody from Chemicon (Billerica, Mass.), and α-tubulin from Sigma-Aldrich (St. Louis, Mo.) (that served as loading control for all Western blots).

For tissue Western blot, whole calvaria were isolated from P1 newborn pups, as described above, and snap frozen in liquid nitrogen. For protein extraction, whole calvaria were homogenized using a Polytron hand-held tissue homogenizer in RIPA buffer. Protein lysates were quantified using the Biorad Bradford Protein Assay reagent, and Western analysis was performed as described above.

Colony Assay:

For colony formation assay, $0.1 \times 10^6$ cells were plated per well in a cluster-6 well plate for 24 hours. The next day, the cells were infected with a retrovirus either encoding eGFP (MSCV-eGFP) or CRE (MSCV-CRE-eGFP) at an MOI of 10, in the presence of 8 µg/ml polybrene. Twenty-four (24) hours after infection, fresh medium was added to the plate and the cells were incubated for an additional 48 hours (72 hours total from the start of infection). The infected cells were then trypsinized and re-plated at a density of 1000 cells/well in a cluster-6 well plate. The plated were incubated for 7-10 days. Green colonies were visualized and counted under a fluorescence microscope. Colonies were fixed in 20% methanol for 15 minutes at room temperature, and counted after staining with 0.5% crystal violet in 20% methanol.

For rescue of colony forming ability, $0.1 \times 10^6$ cells were plated per well in a cluster-6 well plate for 24 hours. The next day, the cells were infected with a lentivirus either encoding human serum albumin (HSA) control or full-length Sox2 at an MOI of 5, in the presence of 8 µg/ml polybrene. Fresh medium was added the next day, and the cells were harvested 48 hours after infection. To check colony forming ability, $0.1 \times 10^6$ cells were plated per well in a cluster-6 well plate for 24 hours. The next day, the cells were infected with a retrovirus either encoding eGFP (MSCV-eGFP) or CRE (MSCV-CRE-eGFP) at an MOI of 10, in the presence of 8 µg/ml polybrene. Colony formation ability was checked as described above.

DNA Synthesis Assay by BrdU Incorporation:

For DNA synthesis assay, $1 \times 10^4$ cells (eGFP or CRE-eGFP infected) were plated in each chamber of 8-well chamber slides from LabTek (Campbell, Calif.), in DMEM medium supplemented with 10% FCS. The next day, BrdU (4 µg/ml) was added to the cells for 4 hours. The treated cells were fixed in 3.7% paraformaldehyde, and permeabilized with 0.5% Triton in PBS for 5 min, followed by 1.5 M HCl for 15 min. After washing, analysis of BrdU incorporation was performed using an anti-BrdU monoclonal antibody (Amersham Pharmacia Biotech) followed by anti-mouse secondary antibody conjugated with Cy3 (Molecular Probes (Invitrogen), dilution 1:200). Nuclei were stained with a solution of I µg/ml of Hoechst 33342 dye in PBS for 5 min. The fluorescence was visualized using a Leica CTR5000 microscope. The frequency of S phase cells was calculated as a ratio of BrdU positive nuclei to the total Hoechst stained nuclei.

Example 1

Conditional Knockout of the Sox2 Gene in Osteoblastic Lineage

Figure 3A:
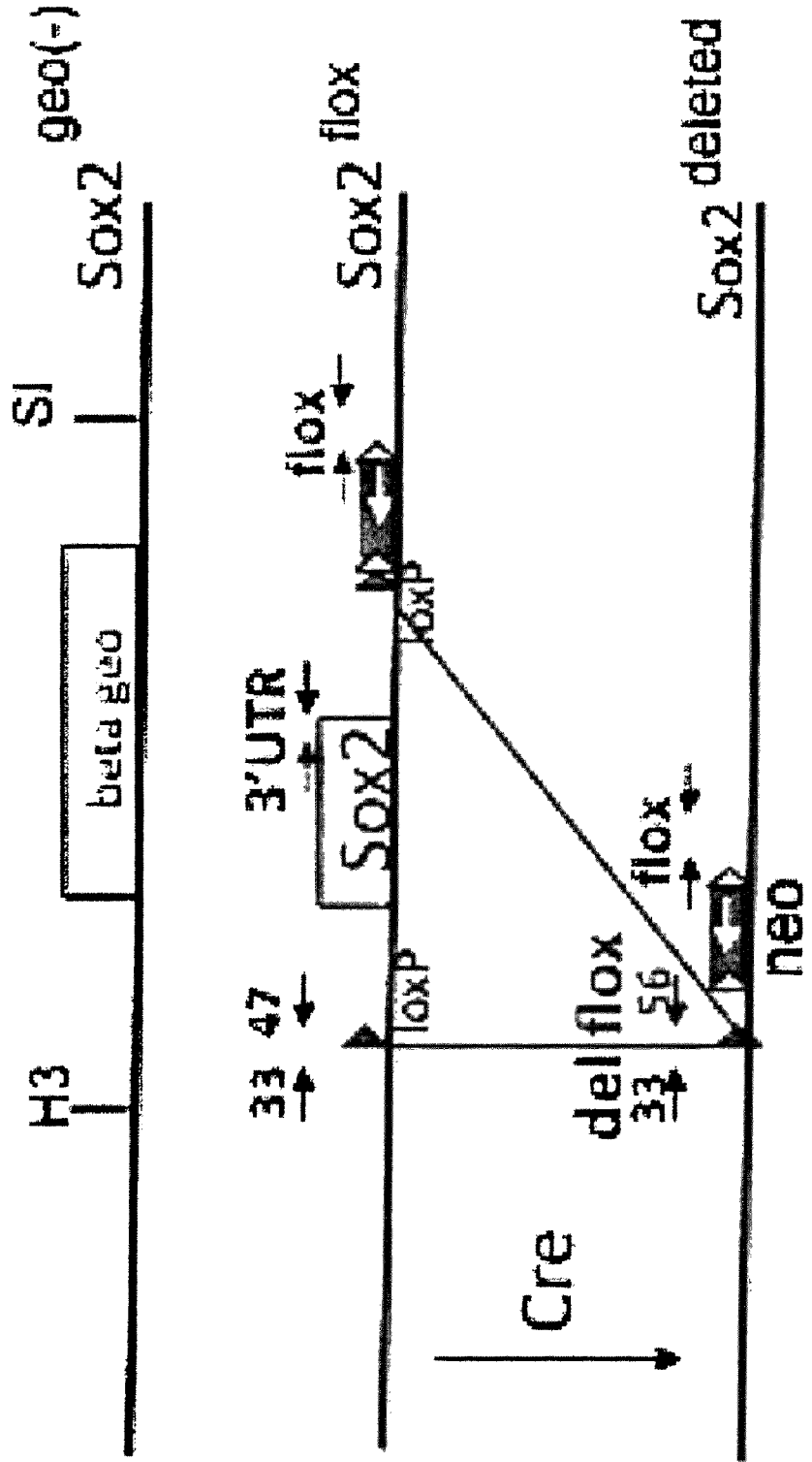
FIG. 3A: Schematic of Sox2 geo, Sox2 flox and Sox2 deleted alleles: The map shows the location of diagnostic primer pairs in the Sox2 alleles. "Beta geo" is the β-galactosidase gene in the Sox2 null (-) allele; the boxes with arrows are the neo gene; triangles are the loxP sites. Other abbreviations include: "3'UTR", the 3' untranslated region, "H3", the HindIII restriction site and "S1", the SalI restriction site.

Since the Sox2 KO is lethal in early embryonic development (2), to precisely define the role of Sox2 induction in the response of osteoblasts to FGF signaling, a conditional knock-out (CKO) of the Sox2 gene in the osteoblastic lineage was created utilizing mice with a $Sox2^{flox/geo}$ genotype (hereafter referred to as $Sox2^{flox/-}$). In these mice, one of the two Sox2 alleles is bracketed by loxP sequences, providing a target for the Cre-recombinase, while the other is replaced by the β-galactosidase (geo) gene, that provides a marker for Sox2 expression and inactivates the Sox2 gene. FIG. 3A shows the location of diagnostic primer pairs in the Sox2 alleles. In FIG. 3A, "beta geo" is β-Galactosidase in the Sox2 null (-) allele, the small box with an arrow is the neo gene and the triangles are the loxP sites. H3 is the HindIII restriction site and S1 is the SalI restriction site. These mice, which are phenotypically normal, were crossed with transgenic mice expressing the Cre-recombinase under the control of the 2.3 kb collagen I promoter (22), which is specifically expressed in the osteoblastic lineage. Cre-recombinase causes excision of the floxed Sox2 gene, and this deletion can be detected by the "del flox" primers, as shown depicted in FIG. 3B. The del flox forward primer sequence 33 is GAC CTA GCC AGA CCC CCT TA. Del flox reverse primer sequence 56 is CGT TGG CTA CCC GTG ATA TT. See, Table 2, above.

The resulting Sox2 CKO mice were initially difficult to study because they died at birth with esophageal atresia, probably due to aberrant expression of the Cre-recombinase in these tissues and the essential role of Sox2 in the development of the foregut. However this phenotype has low penetrance, and at least 50% of the pups survive to adulthood. The surviving CKO mice are dwarf, and have reduced bone density with defects in the formation of trabecular bone. Interestingly, these effects are clearly detected even though these mice are highly mosaic for Sox2 inactivation. At birth, >50% of the calvarial osteoblasts appear to have maintained the Sox2 gene. This result indicates that Sox2 positive cells have a growth advantage over Sox2 null osteoprogenitors.

Figure 3B:
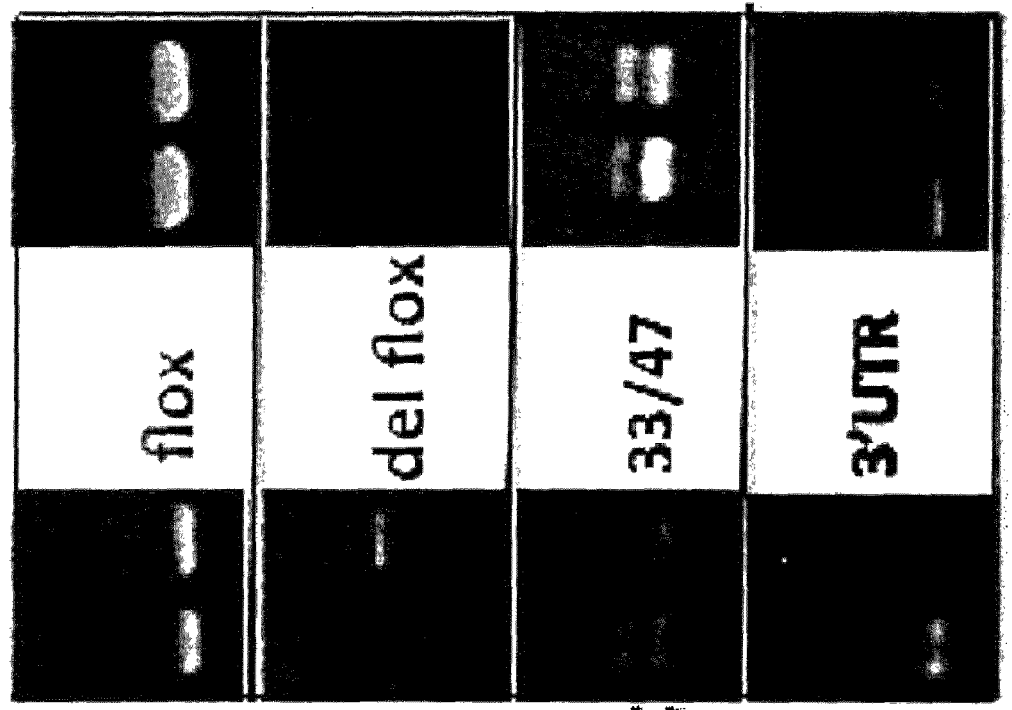
FIG. 3B: PCR analysis of DNA from $Sox2^{flox/-}$ primary osteoblasts following infection with GFP-CRE retrovirus or control virus (GFP): The flox primer pair detects the deleted and undeleted flox alleles. The del flox primer pair detects only the deleted sox2 allele after Cre recombination. The 33/47 primer pair flanks the 5' loxP site and produces two bands in the floxed heterozygous configuration. The lower 480 bp band corresponds to the wild type or beta geo allele, and the upper 560 bp band corresponds to the intact 5'loxP containing Sox2 flox allele. The upper band is not detected when the Cre-mediated deletion has occurred.

When osteoblasts from the P1 calvaria of the mutant Sox2$^{flox/-}$; Cre mice were cultured for 2-3 passages, Sox2 null cells could not be recovered, suggesting that Sox2 deletion is incompatible with osteoblast survival in culture. To determine whether this hypothesis was correct, freshly cultured Sox2$^{flox/-}$ osteoblast populations were infected with a Cre-expressing retrovirus, to force Sox2 excision. Sox2$^{flox/-}$ primary osteoblasts were infected with GFP or GFP-CRE retrovirus. DNA was extracted from passage I and passage 4 cells and PCR was performed with the indicated primers; the results are shown in FIG. 3B. The flox primer pair detects the deleted and undeleted flox alleles. The del flox primer pair detects only the deleted sox2 allele after Cre recombination. As shown in FIG. 3B, the 33/47 primer pair flanks the 5' loxP site and produces two bands in the foxed heterozygous configuration. The lower 480 bp band corresponds to the wild type or beta geo allele, and the upper 560 bp band corresponds to the intact 5' loxP-containing Sox2 flox allele. The upper band is not detected when the Cre-mediated deletion has occurred (FIG. 3B). This band reappears in passaged cells indicating that the undeleted Sox2 allele containing cells are selected upon passaging. The 3'UTR primer pair lies within the Sox2 gene and is not detected upon Cre recombination. This band also reappears after passaging, indicating that Sox2-containing cells have a survival advantage. This experiments showed that Sox2 excision had taken place in a majority of the cells by PCR analysis, but after 2-3 passages in culture only Sox2 positive cells could be detected (FIG. 3B).

Example 2

Colony Assay

To facilitate biochemical and genetic experiments that are difficult to perform in primary cultures, which have a limited life span, several lines of Sox2$^{flox/-}$ osteoblasts were created by immortalizing them with Polyoma large T antigen (PyLT). PyLT inactivates the Rb proteins, but not p53. As previously reported (3), PyLT immortalized osteoblasts are still capable of differentiating into mature osteoblasts in culture, although this process is slightly slower than in primary osteoblasts. Several independent clones of immortalized Sox2$^{flox/-}$ cells were infected with a Cre-virus carrying the green fluorescent protein (GFP) gene, and tested for the ability to form colonies (FIGS. 4A-4C). As shown in the Western blot in FIG. 4A, CRE virus-infected osteoblasts (white box) demonstrate knockout of Sox2 protein 72 hours after CRE infection in clones of Sox2$^{flox/flox}$ (F/F) or Sox2$^{flox/-}$ (F/-), but not in wild type (WT) cells. Anti-tubulin antibody was used as loading control.

A colony assay was performed to determine whether knockout of the Sox2 gene by CRE retrovirus affected osteoblast survival and proliferation. WT or Sox2$^{flox/-}$ immortalized osteoblast clones were infected in triplicate with a retrovirus construct expressing either GFP alone or the Cre recombinase and GFP from an IRES sequence. Colonies on triplicate plates were counted by crystal violet staining. FIG. 4B shows a graph of the results of the colony assay. The percent (%) of colonies obtained in CRE infection are plotted as a percentage of the colonies in the corresponding GFP infection (100%) in five independent Sox2$^{flox/-}$ clones (F/-1-5) and one Sox2$^{flox/flox}$ clone (F/F(2). The number of colonies obtained was drastically reduced (70-90%) with respect to those produced by a control retroviral infection (no Cre), and again all surviving clones were Sox2 positive.

Examination of these cell populations 2-3 days after infection under a fluorescence microscope (10× magnification) showed extensive morphological changes with the appearance of numerous cells with a "flat", senescent-like morphology, and substantial inhibition of proliferation (FIG. 4C). Infection of wild type osteoblasts with the Cre-virus had no deleterious effect, and infection of Sox2$^{flox/-}$ fibroblasts, which do not express Sox2, produced excision of the Sox2 gene, but Sox2 null fibroblasts could be easily maintained in culture.

Example 3

Rescue Assay

Figure 5:
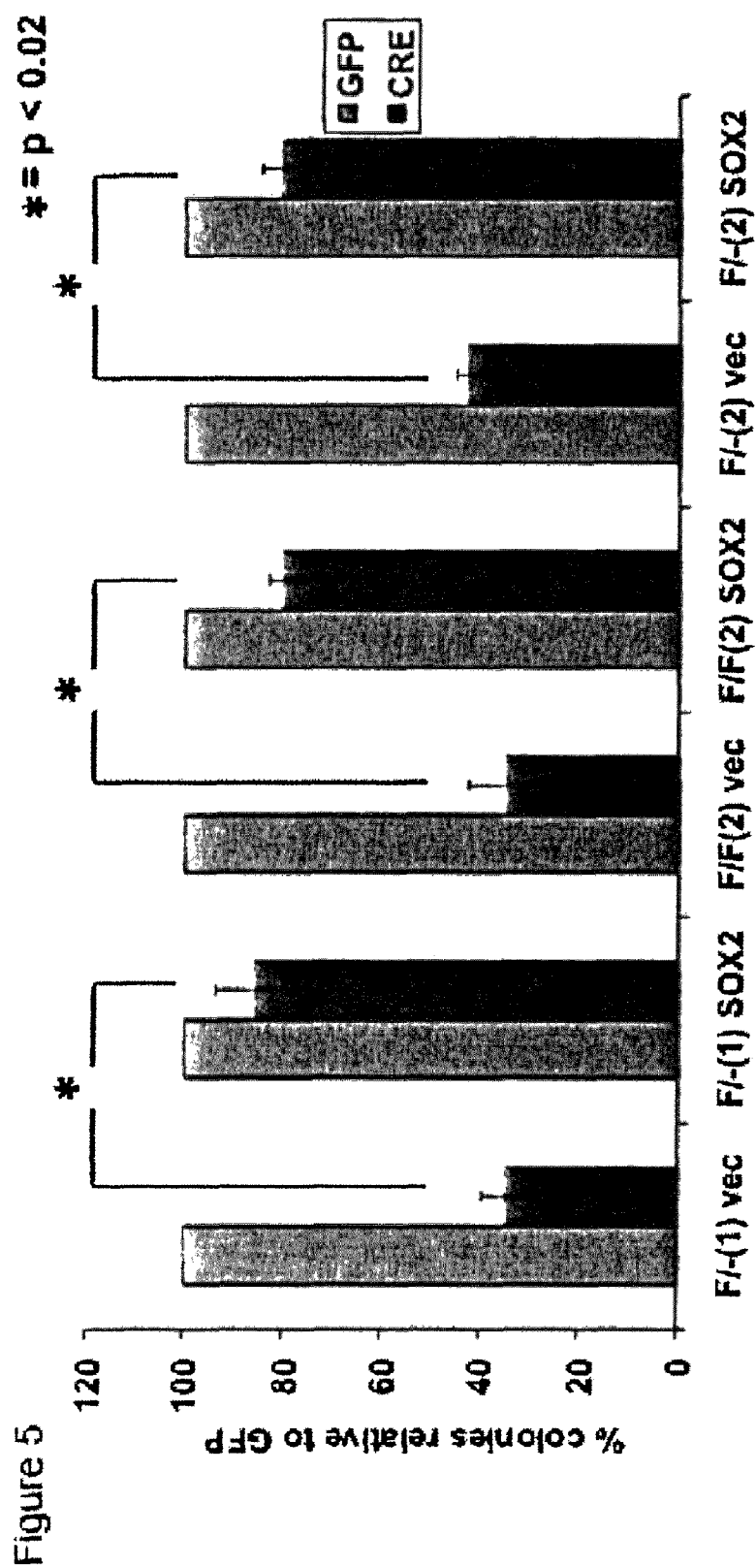
FIG. 5: Expression of transgenic Sox2 rescues the survival of cells in which endogenous Sox2 is deleted: Clones F/-(1), F/-(2) and F/F(2) bearing $Sox2^{flox/-}$ or $Sox2^{flox/flox}$ were transduced with a lentivirus vector carrying Sox2 or a lentivirus control (vec). The graph shows the percent (%) of colonies in the CRE infection in each group relative to the corresponding GFP infection controls (100%).

To conclusively demonstrate that the inhibition of proliferation induced by Cre-mediated excision of the Sox2 gene in Sox2$^{flox/-}$ osteoblasts did not result from DNA damage or other unforeseen effects of Cre expression, a "transgenic" copy of the Sox2 gene or vector control was introduced into three clones of immortalized Sox2$^{flox/-}$ or Sox2$^{flox/flox}$ (F/- or F/F, respectively) clones, F/-(1), F/-(2) and F/F(2), using lentivirus-mediated transduction (FIG. 5). Transgenic Sox2 expression was confirmed by Western analysis.

Sox2 or vector alone (control) pools were then infected with either GFP (blue) or CRE (red) retrovirus, and cells were plated in triplicate for colony formation. The reduction in colony formation by CRE-mediated excision was rescued in cells expressing Sox2 from the lentivirus. The percent of colonies in the CRE infection is shown relative to the corresponding GFP infection (100%). The residual colonies in CRE infected plates were not green, thus representing a background of uninfected cells, while colonies in the CRE-GFP-Infected Sox2 transgenic plates expressed GFP. When these cells were infected with the Cre-virus, the endogenous Sox2 gene was excised, but no detectable inhibition of proliferation or colony formation was observed, showing that constitutive expression of Sox2 abolishes the detrimental effects of the inactivation of the endogenous Sox2 gene.

Discussion

In summary, it is shown here that Sox2 plays a role in the self renewal of a population of uncommitted, osteoprogenitor cells, and that its sustained expression marks these cells for the commitment to the osteoblastic lineage and maintains their proliferation. These data show that Sox2 inactivation is incompatible with sustained proliferation of immature osteoblasts in culture, and the observation that calvaria from newborn Sox2$^{flox/-}$; Cre mice contain an osteoblast population composed mainly of Sox2 positive cells suggest that this may be true also in vivo. Given the well established role of Sox2 in the maintenance of "sternness" in ES cells, in the eye and the CNS (2), it is quite likely that Sox2 plays a similar role in the maintenance of the osteoblastic lineage, and that "osteoblast" cell populations may consist of cells with an intermediate multi/unipotent program of gene expression or contain a proportion of multipotent, Sox2 positive, stem cells that are responsible for their expansion in culture.

Accordingly, Sox2 inactivation would lead to cessation of proliferation and/or terminal differentiation. This notion is also consistent with the finding that FGF signaling, which induces Sox2 expression, promotes osteoblast proliferation and blocks their differentiation (3), and that both FGF signaling and Sox2 overexpression can increase the proliferation of MSCs from which the osteoblastic lineage is derived, while maintaining their osteogenic ability (4,13).

Example 4

Paper Example 1

Screening Assay

The screening assay is performed in 96 well plates. PyLT-immortalized Sox2$^{flox/-}$ osteoblast populations are infected with high titer Cre-virus to delete the Sox2 gene. 80-90% of the cell population is infected using this method and Sox2 excision is extremely efficient. The efficiency of Sox2 excision is determined by PCR analysis of the cell DNA using specific Sox2 primers, as well as by GFP expression. The primers used for Sox2 excision are described above.

The Cre-virus infection is performed in the presence of a screening compound in triplicate wells. Cells are harvested at 24, 48 and 72 hours after infection. These time points, which are slightly long for typical RT-PCR analysis, are useful because of the relatively long half-life of the Sox2 protein (12-16 hrs). Controls are uninfected cells, and cells infected with a GFP (no Cre) retrovirus. To test each screening compound, 2-3 independent clones of immortalized Sox2$^{flox/-}$ osteoblasts are used. Following infection in the presence of each screening compound, cell growth or colony formation is assessed after 7-10 days.

Screening compounds that rescue the Sox2 defect (i.e., allow for the immortalized cells to survive Sox2 inactivation) are then rescreened and tested for osteogenic capacity. In this assay, Sox2 responsive genes identified by microarray may be used as a read-out to monitor the screening assay.

Specifically, these Sox2 responsive gene expression levels in wild-type cells are quantified by PCR, to create a Sox2 gene "expression profile." The gene expression level or expression profile of a Sox2 deficient cell (a cell in which Sox2 is inactivated), following contact with the screening compound is compared to the gene expression level or expression profile of the wild-type cell. A screening compound is determined to be successful (i.e., to be capable of inducing bone growth) if the gene expression level or expression profile of the Sox2 responsive gene in a Sox2 deficient cell is substantially similar to the gene expression level or expression profile in a wild-type cell following contact with the screening compound.

Paper Example 2

Screening Assay with Sox2 Gene Targets

Sox2 gene targets are identified by microarray analysis, and then compounds that directly activate or repress the expression or function of these target genes are identified by an assay that utilizes cells in which at least one Sox2 gene target is inactivated. Compounds that are identified to activate or repress the expression of Sox2 gene targets are determined to regulate bone growth.

Paper Example 3

Screening Assay Using Bone Marrow-Derived MSCs

Bone marrow (BM)-MSCs are derived from femurs and tibia of 4-week old mice. Bones are trimmed and cleaned under sterile conditions, and bone ends are cut of The BM is flushed twice with α-MEM and 10% FCS. The flushed BM cells are centrifuged for 5 minutes at 1500 rpm and then the media is aspirated. The cell pellet is resuspended and then lysed in 1 ml red blood cell lysis buffer (Sigma-Aldrich) for 5 min and neutralized with culture medium. Cells are strained through a 70 micron strainer (BD Biosciences), recentrifuged and plated in a 6-well plate for culture.

MSCs are induced to differentiate into the osteoblastic or adipocyte lineage using established protocols, and the expression of Sox2, as well as differentiation markers characteristic of each lineage, are measured at time intervals. BM-MSCs are cultured at $2 \times 10^6$ cells per 10-cm square well in α-MEM supplemented with 15% fetal calf serum (FCS). Upon confluency, ascorbate-2-phosphate (ascorbic acid 100 µg/ml) and 4 mM beta glycerophosphate are added and cells are cultured for up to 35 days with medium changed every 3 days. Alizarin Red staining (mineralization) is performed after 21-35 days. Differentiation is monitored by staining for alkaline phosphatase activity (Sigma-Aldrich) according to the manufacturer's protocol.

To induce adipogenic differentiation, cells are cultured in adipogenic differentiation medium consisting of DMEM with 10% serum supplemented with 1 µM dexamethasone and 0.5 mM methyl-isobutylxanthine, insulin (1 µg/mL), and 100 µM indomethacin for 2 weeks. Differentiation is monitored by staining with Oil Red (Fisher-Biotech) according to the manufacturer's protocol.

BM-MSCs derived from BM of Sox2$^{flox/-}$; Cre mice are used to study the role of Sox2 in MSC self-renewal and/or differentiation.

Using BM-MSCs, it is determined whether proliferation in culture favors Sox2 positive cells, and whether osteogenic differentiation depends on the expression of the Sox2 gene.

In conclusion, the studies reported herein provide methods for identifying bone anabolic agents. The compound screening assay of the present invention provides novel methods for identifying bone anabolic agents. The methods disclosed herein employ the present discovery that the transcription factor Sox2 plays a critical role in the pathways that maintain the self-renewal capacity of osteoprogenitor cells, a critical step in the process of bone formation.

Primary High throughput Survival Screening Assay

We have developed a 96-well format, cell-based screen using two Sox2 foxed cell lines (F/F and F/-). The approximate doubling time of F/F and F/- lines are 18 hours for F/F cells and 17 hours for F/- cells. In these cell lines, deletion of the endogenous Sox2 leads to a drastic reduction in the ability to form colonies (greater than 80% reduction in colony formation). Deletion of the endogenous Sox2 gene is achieved by infection using a lentivirus vector carrying either GFP (control) or the Cre recombinase gene that acts to excise the floxed Sox2 allele. The infection efficiency of the lentivirus is routinely greater than 90% of all cells ensuring near-complete deletion of the Sox2 gene as described in BasuRoy et al, 2010. Following 72 hours after infection, the cell lines were plated in 100 µl per well of regular DMEM medium containing 10% fetal bovine serum in clear, flat-bottomed 96-well plates (Corning Glass, Corning, N.Y.). We incorporated DMSO (Sigma Aldrich, St. Louis, Mich.) as a "negative" control, as DMSO does not alter the efficacy of Cre-dependent lethality of the osteoblasts and also, because most commercially available small molecule libraries use DMSO as a solvent for the compounds. As a "positive" control, we included 10 µM SB431542, (commercially available from Sigma, St. Louis, Mo.), a compound that has been previously shown to bypass the requirement of Sox2 in the reprogramming of iPSCs (7,32). We have determined that in our osteoblast system, we are able to rescue to loss of colony forming ability of Sox2-depleted osteoblasts using 10 μM SB431542. After 48 hours in DMSO or drug, 10 μl of CellTiter-Blue® Cell Viability Assay (Promega, Wis.) was added to each well. The CellTiter-Blue® Cell Viability Assay is a fluorescence-based assay for measuring cell viability, and has an excellent Z' factor[1]. It has been employed for HTS. After one hour of incubation with the reagent, fluorescence was read using a Wallac Plate Reader (Perkinelmer, Waltham, Mass.). Z' factor and z score for each plate was calculated for each cell line at different cell plating concentrations as described (28, 29). All statistical analysis was carried out using SPSS software. Typical results are presented in FIG. 6.

[1] Z factor is defined in the Appendix which follows Example 5.

Figure 6A:
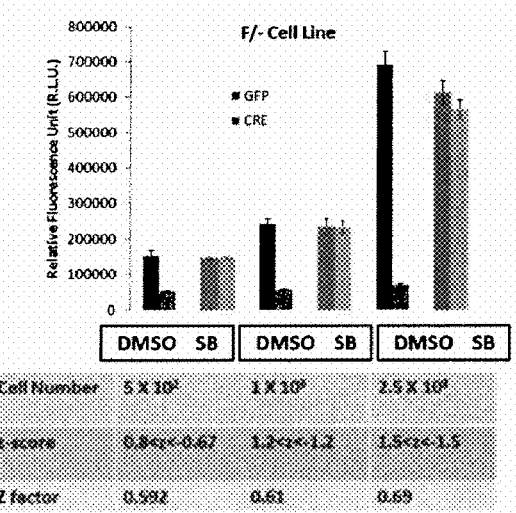
FIGS. 6A and B: Fluorescence based cell viability assay on control (GFP) or Sox2-deleted (CRE) cells in the presence of vehicle (DMSO) or SB431542 in two independent Sox2-foxed cell lines, clones F/- (A) and F/F (B). Two independent Sox2-floxed cell lines were plated at different densities after CRE and GFP lentivirus infection in clear, flat-bottomed 96-well plates. Cell viability was determined using the CellTiter Blue Assay. Fluorescence values were determined using a Wallac Plate Reader and statistical analysis was carried out using SPSS software.
Figure 6B:
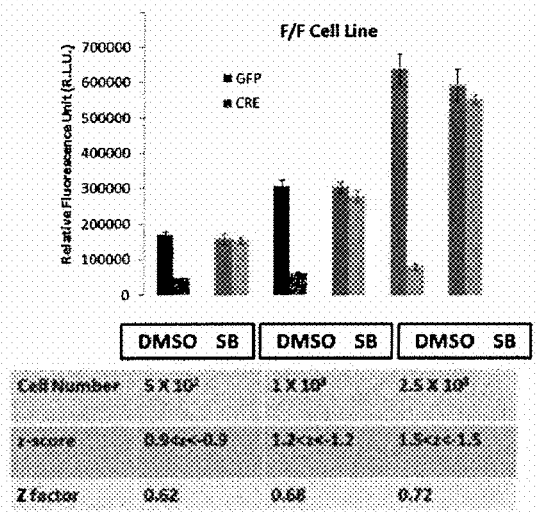
FIG. 6 depicts both the cell lines gave highly comparable values for each of the cell densities plates. Z factor and z-score for each plate and for the different densities plated are indicated. The Z' factor was calculated using GFP-infected and SB431542-treated, in both the GFP- and CRE-infected samples. Both cell lines exhibit Z' factors of greater than 0.5. For a robust HTS assay free from systematic errors, with the best Z score and dynamic range, a plating cell density of $2.5 \times 10^3$ cells/well is used. Mean differences between GFP (control) and CRE-infected cells is in the range of 5-6 fold providing a broad dynamic range for the assay.

In FIG. 6, two Independent Sox2-floxed cell lines, clones F/- (1) and F/F (2) were plated at different densities after CRE and GFP Lentivirus Infection in clear, flat-bottomed 96-well plates. DMSO or SB43152 (10 □M) (Sigma, St Louis Mo.; cat number S4317). was added the next day. Cell viability was determined using the CellTiter Blue Assay (Promega) 48 hours later. Fluorescence values were determined using a Wallace Plate Reader and statistical analysis was carried out using SPSS software.

As seen in FIG. 6, both cell lines gave highly comparable values for each of the cell densities plates. Z factor and z-score for each plate and for the different densities plated are indicated. The Z' factor was calculated using GFP-infected and SB431542-treated cells, in both the GFP- and Cre-infected samples. Both cell lines exhibit Z' factors of greater than 0.5. For a robust HTS assay free from systematic errors, with the best Z score[2] and dynamic range, a plating cell density of $2.5 \times 10^3$ cells/well is used. Mean differences between GFP (control) and Cre-infected cells is in the range of 5-6 fold providing a broad dynamic range for the assay.

[2] Z factor is defined in the Appendix which follows example 5.

Cell counts performed in parallel wells showed that this 5-6 fold difference in GFP and Cre infected cells is also reflected in cell number counts at 96 hours. Thus the assay has an excellent range to enable identification of varying degrees of rescue.

The approximate analysis time for the plate reader for each plate is approximately 30 seconds. Data obtained from the primary screen will be analyzed using HTS-Corrector Software (28). Fluorescence readout from each well will be normalized by converting to a z score. The raw mean and standard deviation (S.D.) will be calculated from all test wells of a single plate. All data points that are more than three S.D.s away from the raw mean are excluded. The corrected mean ($x_c$) and the S.D.(s) of the filtered data will be calculated. The final z score for each plate for the assay will be calculated using the formula $z=(x_i-x_c)/s$, where x, is the raw measurement for the ith compound in the plate. Based on our assessments, compounds with a z-score of >+1.5 and <-1.5 will be designated as hits. Any compound that shows a positive z-score of greater than 1.5 will be considered to be a potential "hit". DMSO and SB431542 will serve as negative and positive control controls respectively and will be employed in all statistical analysis. This protocol routinely yields a Z' factor of 0.7. We will perform the initial small molecule screens using commercially available small drug libraries, LOPAC 1280 (Sigma, St Louis, Mo.) and a library of FDA-approved drugs, BIOMOL (Enzo Life Sciences), Plymouth Meeting, Pa.).

The purpose of the secondary screen is to further validate targets from the primary screen. It is known in the art that the Connective Tissue Growth Factor (CTGF) gene is a target of Sox2 and is suppressed in osteoblasts in which Sox2 is over expressed (our unpublished data). Conversely, levels of CTGF are dramatically up-regulated following the deletion of Sox2 in osteoblasts (unpublished results). Thus, CTGF levels are inversely related to Sox2 expression and can serve as a sensitive read-out for Sox2 levels. A stable osteoblast cell line derived from the F/- cell line will be established to express a Firefly luciferase construct under the control of the CTGF promoter. Additionally, the cell line will also express the Renilla luciferase gene under the control of the thymidine kinase promoter. The Renilla luciferase gene serves as a negative control, GFP-control and CRE-virus infected F/- osteoblasts expressing the Firefly-CTGF and the Renilla control vectors will be plated at a density of $2.5 \times 10^3$ cells/well in a flat-bottomed, white 96-well plate (Corning, Corning, N.Y.). The next day, either DMSO or different concentrations of SB431542 (2, 5 and 10 μM) will be added. Luciferase activity will be read after 24, 48 and 72 hours after drug treatment. Fifteen microliters of Dual-Glo (Promega, Wis.) will be added to each well and incubated at room temperature for 15 minutes and Luciferase units will be measured. Following this measurement, 15 μl of Stop-and-Glo reagent Promega, Wis. will be added to each well, incubated at room temperature for 15 minutes and Renilla activity will be measured using the Perkin-ElmerTriLux reader. After estimating the Firefly/Renilla ratio, the raw mean and standard deviation (S.D.) will be calculated from all test wells of a single plate. All data points that are more than three S.D.s away from the raw mean will be excluded. The corrected mean ($x_c$) and the S.D.(s) of the filtered data will be calculated. The final z score for each plate for the assay will be calculated using the formula $z=(x_i-x_x)/s$, where $x_i$ is the raw measurement for the ith compound in the plate. Based on preliminary screens, compounds with a z-score of >+1.5 and <-1.5 will be designated as confirmed hits. Any compound that shows a positive z-score of greater than 1.5 will be considered to be a confirmed "hit". DMSO and SB431542 will serve as negative and positive controls respectively and will be employed in all statistical analysis.

Luciferase units are expected to increase in CRE-infected cells and decrease in the presence of positive hits (identified from primary screen) that mimic Sox2.

In addition to a secondary screen, a stringent "tertiary" counter screen may also be used. In this screen, akin to the colony-forming assay described in FIG. 4B and in Basu Roy etal, 2010, GFP and CRE-lentivirus infected F/- osteoblasts will be plated in clear, flat-bottomed 96-well plates (Corning, Corning, N.Y.) at a density of 50 cells/well in 10 μM of a "potential" hit compound and incubated for 48 hours. Following the incubation period, the cells will be fixed in 4% paraformaldehyde and imaged using the Molecular Devices Discovery1/Image Express (WCMC). This tertiary screen will be critical since it will eliminate false positives obtained in the secondary screen.

References for Examples 1-4

1. Mansukhani, A, Ambrosetti, D, Holmes, G, Cornivelli, L, et al. (2005) Sox2 induction by FGF and FGFR2 activating mutations inhibits Wnt signaling and osteoblast differentiation. J Cell Biol. 168:1065-1076.
2. Niwa H. (2007) How is pluripotency determined and maintained? Development. 34(4):635-46.

3. Mansukhani A, Bellosta P, Sahni M, and Basilico C. (2000) Signaling by FGF and FGFR-2 activating mutations induces apoptosis and blocks mineralization in osteoblasts. J. Cell Biol. 149:1297-1308.
4. Go M J, Takenaka C, Ohgushi H. (2008) Forced expression of Sox2 or Nanog in human bone marrow derived mesenchymal stem cells maintains their expansion and differentiation capabilities. Exp Cell Res. 314(5):1147-54.
5. Fromigué O, Modrowski D, Marie P J. (2004) Growth factors and bone formation in osteoporosis: roles for fibroblast growth factor and transforming growth factor beta. Curr Pharm Des. 10(21):2593-603.
6. Dunstan C R, Boyce R, Boyce B F, Garrett I R, et al. (1999) Systemic administration of acidic fibroblast growth factor (FGF-1) prevents bone loss and increases new bone formation in ovariectomized rats. J Bone Miner Res. 14(6):953-9.
7. Shi Y, Desponts C, Do J T, Hahm H S, et al. (2008) Induction of pluripotent stem cells from mouse embryonic fibroblasts by Oct4 and Klf4 with small-molecule compounds. Cell Stem Cell. 3(5):568-74.
8. Ambrosetti D, Holmes G, Mansukhani A, Basilico C. (2008) Fibroblast growth factor signaling uses multiple mechanisms to inhibit Wnt-induced transcription in osteoblasts. Mol Cell Biol. 28(15): 4759-71.
9. Yuan H, Corbi N, Basilico C, Dailey L. (1995) Developmental-specific activity of the FGF-4 enhancer requires the synergistic action of Sox2 and Oct-3. Genes Dev. 9(21): 2635-45.
10. Ambrosetti D-C, Schöler H R, Dailey L, and Basilico C. (2000) Modulation of the activity of multiple transcriptional activation domains by DNA-binding domains mediates the synergistic action of Sox2 and Oct-3 on the FGF-4 enhancer. J. Biol, Chem. 275:23387-23397.
11. Dailey, L, and Basilico, C. (2001) Coevolution of HMG domains and homeodomains and the generation of transcriptional regulation by Sox/POU complexes. J. Cell. Physiol. 186:315-3228.
12. Dailey, L, Ambrosetti, D, Mansukhani, A, and Basilico, C. (2005) Mechanisms underlying differential responses to FGF signaling. Cytokine Growth Factor Reviews. 16:233-247.
13. Choi S C, Kim S J, Choi J H, Park C Y, et al. (2008) Fibroblast growth factor-2 and -4 promote the proliferation of bone marrow mesenchymal stem cells by the activation of the PI3K-Akt and ERK1/2 signaling pathways. Stem Cells Dev. 2008 17(4):725-36.
14. Dailey L, Laplantine E, Priore R, and Basilico C. (2003) A network of transcriptional and signaling events activated by FGF to induce chondrocyte growth arrest and differentiation. J Cell Biol. 161:1053-1066.
15. Tay Y, Zhang J, Thomson A M, Lim B, et al. (2008) MicroRNAs to Nanog, Oct4 and Sox2 coding regions modulate embryonic stem cell differentiation. Nature. 455 (7216):1124-8.
16. Card D A, Hebbar P B, Li L, Trotter K W, et al. (2008) Oct4/Sox2-regulated miR-302 targets cyclin D1 in human embryonic stem cells. Mol Cell Biol. 28(20):6426-38.
17. Yaragatti M, Basilico C, Dailey L. (2008) Identification of active transcriptional regulatory modules by the functional assay of DNA from nuclosome-free regions. Genome Res. 18(6): 930-8.
18. Gutierrez G M, Kong E, Sabbagh Y, Brown N E, et al. (2008) Impaired bone development and increased mesenchymal progenitor cells in calvaria of RB 1-/- mice. Proc Natl Acad Sci U S A. 105(47):18402-7.
19. Bonyadi M, Waldman S D, Liu D, Aubin J E, et al. (2003) Mesenchymal progenitor self-renewal deficiency leads to age-dependent osteoporosis in Sca-1/Ly-6A null mice. Proc Natl Acad Sci U S A. 100(10):5840-5.
20. Ellis P, Fagan B M, Magness S T, Hutton S, et al. (2004) SOX2, a persistent marker for multipotential neural stem cells derived from embryonic stem cells, the embryo or the adult. Dev Neurosci. 26(2-4):148-65.
21. Berman S D, Cabo E, Landman A S, Danielian P S, et al. (2008) Metastatic osteosarcoma induced by inactivation of Rb and p53 in the osteoblast lineage. Proc Natl Acad Sci U S A. 105(33):11851.
22. Dacquin R, Starbuck M, Schinke T, Karsenty G. (2002) Mouse alpha1(I)-collagen promoter is the best known promoter to drive efficient Cre recombinase expression in osteoblast. Dev Dyn. 224(2):245-51.
23. Bilezikan J P, Raisz L G and Rodan G A. Chapter 4: Mesenchymal Stem Cells and Osteoblast Differentiation. Principles of Bone Biology. Vol. I. 2nd Edition, 2002.
24. Steenhuis P, et. al. (2008) Cell surface expression of stem cell antigen-1 (Sca-1) distinguishes osteo-, chondro-, and adipoprogenitors in fetal mouse calvaria. Calcif Tissue Int 82: 44-56.
25. Grigoriadis A E, et. al. (1998) Differentiation of muscle, fat, cartilage, and bone from progenitor cells present in a bone-derived clonal cell population: effect of dexamethasone. J. Cell Biol. 106:2139-51.
26. Mundy G R. (2007) Osteoporosis and Inflammation. Review. Nutr. Rev. 65:S147-51.
27. Gonzalez R, et. al. (2007) Pluripotent marker expression and differentiation of human second trimester Mesenchymal Stem Cells. Biochem Biophys Res Commun 362(2): 491-7.
28. Malo, N., J. A. Hanley, S. Cerquozzi, J. Pelletier, and R. Nadon. 2006. Statistical practice in high-throughput screening data analysis. Nat Biotechnol 24:167-75.
29. Zhang J H, Chung T D, Oldenburg K R, A Simple Statistical Parameter for Use in Evaluation and Validation of High Throughput Screening Assays. J Biomol Screen. 1999; 4(2):67-73).
30. Lewiecki, E. M. 2009. Managing osteoporosis: challenges and strategies. Cleve Clin J Med 76:457-66.
31. Basu-Roy, U., D. Ambrosetti, R. Favaro, S. K. Nicolis, A. Mansukhani, and C. Basilico. 2010. The transcription factor Sox2 is required for osteoblast self-renewal. Cell Death Differ. May 21 (Epub ahead of print) PMID: 20489730.
32. Ichida, J. K., J. Blanchard, K. Lam, E. Y. Son, J. E. Chung, D. Egli, et al. 2009. A small-molecule inhibitor of tgf-Beta signaling replaces sox2 in reprogramming by inducing nanog. Cell Stem Cell 5:491-503.
33. Masui, S., Y. Nakatake, Y. Toyooka, D. Shimosato, R. Yagi, K. Takahashi, et al. 2007. Pluripotency governed by Sox2 via regulation of Oct3/4 expression in mouse embryonic stem cells. Nat Cell Biol 9:625-35.

Example 5

Introduction

Osteoporosis—A growing public health problem: Osteoporosis is a public health threat for an estimated 44 million people in the US (12). About 10 million Americans (8 million women and 2 million men) are living with osteoporosis, while 34 million Americans or 55% of people over 50 years of age have low bone mass (osteopenia), which increases the risk of developing osteoporosis (12). Additionally, chronic steroid use and many auto inflammatory conditions also lead to bone loss (13). According to the National Osteoporosis Foundation, half of all women over 50 will suffer a fracture in her lifetime and 20% of senior citizens who suffer hip fracture require subsequent long term care (12). Healthcare costs for osteoporosis are estimated at 20 billion annually (14). The Surgeon General's Report suggests that without a concerted effort to address osteoporosis, 1 in 2 Americans over age 50 will have or be at high risk for developing osteoporosis in 2020 when over 61 million may be at risk for osteoporosis and osteopenia (14, 15). Given this forecast, there is an urgent need for the development of novel anti-osteoporotic medication. Osteoporosis is a severe chronic disease that involves progressive bone loss leading to fragile bones and increased susceptibility to fractures in the elderly and in postmenopausal women. The currently accepted model for osteoporosis development is the presence of an imbalance between the activity of osteoblasts (the bone forming cells) and that of the osteoclasts (cells that resorb bone) (1). Despite considerable advances in bone biology, current osteoporosis treatments are targeted towards decreasing osteoclast activity. While they have been shown to prevent bone loss, most osteoclast inhibitors have limited ability to enable new bone formation. Anti-resorptive therapies administered over 2-3 years increase bone mineral density by only 2-8%. Recently, there has been focus on developing a new class of anti-osteoporotics, namely bone anabolics that promote osteoblast function and act by replenishing lost bone (2). Bone anabolic agents are expected to be more effective at combating bone loss. The Food and Drug Administration (FDA) has approved the use of a single bone anabolic agent, recombinant parathyroid hormone (PTH/teraparatide) sold under the name of Forteo and manufactured by Eli Lilly, for the treatment of cases of severe osteoporosis (3). However, as with many recombinant proteins, the use of Forteo is limited as it is prohibitively expensive, needs to be injected, and is associated with several risks (3). Thus, there is a large unmet need to develop bone anabolics that are effective and affordable, with minimal side effects.

Bone development is a complex process that involves the interplay of many cell types, but cells of the osteblast lineage are responsible for building bone. The Fibroblast Growth Factor (FGF) pathway, Wnt, BMP, Notch and Hedgehog are some of the critical signaling pathways that regulate bone development through their action on osteoblasts (4). We have previously shown that sustained FGF signaling increases proliferation of immature osteoblasts and blocks the differentiation process (5). We have also demonstrated that Sox2, a member of the SRY-related HMG box family of transcription factors, is induced by FGF signaling in immature osteoblasts (6). FGF antagonizes Wnt signaling, an important pro-differentiation signal, in part through the induction of Sox2 (6, 7). Sox2 is an essential gene early in embryonic development and is a well-known player in embryonic stem cells (ES) where it is required to maintain self-renewal and pluripotency (8). We originally identified a binding partner for Oct-4 in ES cells where it regulates the expression of ES-cell specific genes (9). Recently, Sox2 has been identified as one of the four genes required for reprogramming somatic cells to iPS cells (induced pluripotent cells) (10). We have generated a Sox2 conditional knockout (bone-specific) mouse model (Sox2 CKO), and have uncovered a previously unknown role for this transcription factor in the osteoblast lineage. Sox2 CKO mice have reduced bone density mimicking early osteoporosis, and inactivating Sox2 in in vitro osteoblast cultures decreases osteoblast proliferation (11). These data indicate that Sox2 is required for maintenance of immature oteoblasts.

We have shown that Sox2-deleted osteoblasts are unable to sustain proliferation. In the data presented above, we describe the finding of an assay based on Sox2-deleted cells for the high throughput screening of compounds that can mimic Sox2 and promote survival, in Sox2-null osteoblasts. Such compounds could be good candidates for bone anabolic agents.

In the present example, we describe the development of such a primary screening assay to identify bone anabolic agents by utilizing a high thoroughput screen (HTS) for small molecule agents that can bypass the Sox2 requirement and restore osteoblast survival in Sox2-deleted cells.

References for Example 5

1. Lewiecki, E. M. 2009. Managing osteoporosis: challenges and strategies. Cleve Clin J Med 76:457-66.
2. Datta, N. S., and A. B. Abou-Samra. 2009. PTH and PTHrP signaling in osteoblasts. Cell Signal 21:1245-54.
3. Deal, C. 2009. Potential new drug targets for osteoporosis. Nat Clin Pract Rheumatol 5:20-7.
4. Deng, Z. L., K. A. Sharff, N. Tang, W. X. Song, J. Luo, X. Luo, et al. 2008. Regulation of osteogenic differentiation during skeletal development. Front Biosci 13:2001-21.
5. Mansukhani, A., P. Bellosta, M. Salmi, and C. Basilico. 2000. Signaling by fibroblast growth factors (FGF) and fibroblast growth factor receptor 2 (FGFR2)-activating mutations blocks mineralization and induces apoptosis in osteoblasts. J Cell Biol 149:1297-308.
6. Mansukhani, A., D. Ambrosetti, G. Holmes, L. Cornivelli, and C. Basilico. 2005. Sox2 induction by FGF and FGFR2 activating mutations inhibits Wnt signaling and osteoblast differentiation. J Cell Biol 168:1065-76.
7. Ambrosetti, D., G. Holmes, A. Mansukhani, and C. Basilico. 2008. Fibroblast growth factor signaling uses multiple mechanisms to inhibit Wnt-induced transcription in osteoblasts. Mol Cell Biol 28:4759-71.
8. Masui, S., Y. Nakatake, Y. Toyooka, D. Shimosato, R. Yagi, K. Takahashi, et al. 2007. Pluripotency governed by Sox2 via regulation of Oct3/4 expression in mouse embryonic stem cells. Nat Cell Biol 9:625-35.
9. Yuan, H., N. Corbi, C. Basilico, and L. Dailey. 1995. Developmental-specific activity of the FGF-4 enhancer requires the synergistic action of Sox2 and Oct-3. Genes Dev 9:2635-45.
10. Takahashi, K., and S. Yamanaka. 2006. Induction of pluripotent stem cells from mouse embryonic and adult fibroblast cultures by defined factors. Cell 126:663-76.
11. Basu-Roy, U., D. Ambrosetti, R. Favaro, S. K. Nicolis, A. Mansukhani, and C. Basilico. 2010. The transcription factor Sox2 is required for osteoblast self-renewal. Cell Death Differ. May 21 (Epub ahead of print) PMID: 20489730.
12. NOF 2009, posting date. Fast Facts on Osteoporosis. [Online.]
13. Weldon, D. 2009. The effects of corticosteroids on bone growth and bone density. Ann Allergy Asthma Immunol 103:3-11; quiz 11-3, 50.
14. Burge, R., B. Dawson-Hughes, D. H. Solomon, J. B. Wong, A. King, and A. Tosteson. 2007. Incidence and economic burden of osteoporosis-related fractures in the United States, 2005-2025. J Bone Miner Res 22:465-75.
15. USDHHS 2004, posting date. Bone Health and Osteoporosis: A Report of the Surgeon General. [Online.]
16. Parfitt, A. M. 2001. The bone remodeling compartment: a circulatory function for bone lining cells. J Bone Miner Res 16:1583-5.

17. Dailey, L., D. Ambrosetti, A. Mansukhani, and C. Basilico. 2005. Mechanisms underlying differential responses to FGF signaling. Cytokine Growth Factor Rev 16:233-47.
18. Niwa, H. 2007. How is pluripotency determined and maintained? Development 134:635-46.
19. Dailey, L., and C. Basilico. 2001. Coevolution of HMG domains and homeodomains and the generation of transcriptional regulation by Sox/POU complexes. J Cell Physiol 186:315-28.
20. Favaro, R., M. Valotta, A. L. Ferri, E. Latorre, J. Mariani, C. Giachino, et al. 2009. Hippocampal development and neural stem cell maintenance require Sox2-dependent regulation of Shh. Nat Neurosci 12:1248-56.

Prophetic Example 4

The assays described herein are used for high throughput screening to identify compounds that can be tested in murine models of osteoporosis to determine their ability to prevent bone loss. Compounds that can mimic the function of a survival factor of the osteoblast lineage represents a unique opportunity for drug discovery and development of new bone anabolics.

Prophetic Example 5

Construction of Sox2-sensitive reporter for the secondary screen The CTGF promoter will be PCR cloned from murine osteoblast cDNA and subcloned in the pGL3-basic luciferase vector (Promega, Madison Wis.). The promoter-luciferase encoding fragment will be subloned into pCDNA 3.1 (Invitrogen, Calif.), which carries a selectable neomycin resistance gene. The pcDNA/CTGF-luciferase will be transfected into Sox2 F/F or Sox2 F/- cells and neomycin resistant stable cells bearing the reporter will be selected. These cells will be infected with GFP or CRE virus and luciferase activity will be measured.

APPENDIX 1

Definition of Z-Score

A z-score is a statistical measure that quantifies the distance (measured in standard deviations) a data point is from the mean of a data set. A z-score is an indication not only whether a given point was above or below average, but also how unusual the measurement is. The z score is calculated as:

$$z = \frac{x - \mu}{\sigma}$$

where: x is a raw measurement of a given point; μ is the mean of the population; σ is the standard deviation of the population. The quantity z represents the distance between the raw score and the population mean in units of the standard deviation. z is negative when the raw score is below the mean, positive when above.

Definition of Z Factor

The Z-factor is a measure of statistical effect size that is defined in terms of four parameters: the means and standard deviations of both the positive (p) and negative (n) controls (, and,). Given these values, the Z-factor is defined as:

$$Z\text{-factor} = 1 - \frac{3(\sigma_p + \sigma_n)}{|\mu_p - \mu_n|}.$$

In practice, the Z-factor is estimated from the sample means and sample standard deviations A Z-factor of 1, ideal. This is approached when there is a large dynamic range with small standard deviations. Z-factors can never actually equal 1.0 and can certainly never be greater than 1.0.

A Z-factor between 0.5 and 1.0 is an excellent assay.

A Z-factor between 0 and 0.5 is marginal.

A Z-factor less than 0 indicates that the signal from the positive and negative controls overlap, rendering the assay essentially useless for screening purposes (29).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

What is claimed is:

1. A method for identifying a compound capable of inducing bone growth, which method comprises the steps of:
   providing a Sox2 deficient cell having a Sox2 defect;
   contacting said cell with said compound; and
   determining if said compound rescued the Sox2 defect following said contacting step, wherein said compound is useful for inducing bone growth if it rescued the Sox 2 defect.

2. A method for identifying a compound capable of inducing bone growth, which method comprises the steps of:
   quantifying at least one Sox2 responsive gene expression level in a wild-type cell;
   providing a Sox2 deficient cell having a Sox2 defect;
   contacting said Sox2 deficient cell with said compound;
   quantifying the gene expression level of at least one Sox2 responsive gene in said Sox2 deficient cell following said contacting step; and
   comparing the gene expression level of said Sox2 responsive gene to the gene expression level of said Sox2 responsive gene obtained from a wild-type cell; wherein said compound is capable of inducing bone growth if the gene expression level of said Sox2 deficient cell is substantially similar to the gene expression level of said wild-type cell.

3. The method of claim 1, wherein said cell is an osteoblast.

4. The method of claim 1, wherein said cell is a mesenchymal stem cell.

5. The method of claim 1, wherein said Sox2 defect is characterized by an inability of said cell to proliferate.

6. The method of claim 1, wherein said Sox2 defect is characterized by an inability of said cell to survive in culture.

7. The method of claim 1, wherein said Sox2 defect is characterized by an inability of said cell to self-renew.

8. The method of claim 1, wherein said Sox2 defect is characterized by an inability of said cell to differentiate into an osteoblast.

9. The method of claim 2, wherein the gene expression level of said at least one Sox2 responsive gene is determined by polymerase chain reaction (PCR).

10. The method of claim 2, wherein the Sox2 deficient cell is an osteoblast.

11. The method of claim 2, wherein the Sox2 deficient cell is a mesenchymal stem cell.

12. The method of claim 2, wherein said Sox2 defect is characterized by an inability of said cell to proliferate.

13. The method of claim 2, wherein said Sox2 defect is characterized by an inability of said cell to survive in culture.

14. The method of claim 2, wherein said Sox2 defect is characterized by an inability of said cell to self-renew.

15. The method of claim 2, wherein said Sox2 defect is characterized by an inability of said cell to differentiate into an osteoblast.

16. The method of claim 1 wherein said assay contains a negative control.

17. The method of claim 16 wherein said assay contains a positive control.

18. The method of claim 2 wherein said assay contains a negative control.

19. The method of claim 18 wherein said assay contains a positive control.

* * * * *

SEQUENCE LISTING

```
<160> NUMBER OF SEQ ID NOS: 14

<210> SEQ ID NO 1
<211> LENGTH: 9503
<212> TYPE: DNA
<213> ORGANISM: Homo sapiens

<400> SEQUENCE: 1
tatatgttta ttctttttat catctggaaa cattcattat agttactgtc actaatcctt      60
cacacttcca aaatctgaca agtttgacat aggaaaaaaa tggggggaaat gtagatgaaa     120 gagtttctat cattttgaaa attgtgttat aaaaattaag atgtctatcc cctctaggaa     180
ttcctatgag ggatccttca cagtctaaag gaaatgaagt ttgacaatgg tacaattcag     240
ttttgaattt ttgctcttac tttctatatc ctaacctttt ccagcttatt tcttgttaat     300
```

```
tgtttttgga aagtatgcaa tgctctttta agggaaaaaa aatcttctaa tgcacttatt      360
taccttcatt tatatgtgtt tgtttctgaa atgaagaatc aagctttggt cattccggaa      420
gtcgtgtagc atgctccaat ttgaagtgac tgagatcttt tgtgacttac agaggagaag      480
gaaatgtttt aaaaattggc ttatgccagt ctccttactc tgaaattctc aattttcttg      540
tattacagga taaatataaa tatcatctca ccaaattgta ccagcattgt cctaaacatt      600
taaattttcc tttatttttg gcctttaaaa ttagaaaatt ttctccagtt gctgcactta      660 gcttttaat tttgttttct tttcacttac cagactactg gtatgatctc tttcactgca       720
gtatgattgc tgctatggtc acttttagag gagattgtgg gaaggttagg atttggagga     780
aacatgacaa aaaagggaag aaaaaaaaaa accttcattt gaccacatct ggctgcttgt      840
atatttaacc agttctagaa ttagaaaacc tttctgtaca ttttcttcta ttttttctcac    900 ttttttcctt acataatgaa attaaaactt ttggagccta cagttgacat ttttcagaaa      960
attgagttat caaggcagta attatttcac ggggagataa aactctcata gccctaactg     1020
tcaaataggg cccttttcag attttaatta caaaataaaa ttagtctgct cttcctcaga    1080
atggtttgtg agtggttaaa cagagctttc ccccaatact ggtggtcgtc aaactctgct   1140
aattagcaat gctgagaaat tccagttaac aaggacattc tccaagactc tgcaggttcc    1200
ctgccgtttg ccttcatttc cataagaaga ttaagagagg aggggaacac actcaaatgc    1260
agatgcagaa aagaagcgtt ttttaacaag catcataata gtaagatgct tggctagttc    1320
tcacctaatt actgcaagtt aaacctctat ttgacactaa gagaaaaaa taagtctaca     1380 gtcccctgtc tccacaaaat tgttagttgg tttcagatat aatacttgag gagtgctgag    1440
gagactttag gagagaaaaa tcaatgtgca agattttgaa ataaaattga gttacactta    1500
acagttaagg cctttgggct agggcctata atagaacaaa ataaaatcag aatattccag    1560
gagtcatgca tttttgttac taactactaa tcttgctcta aaagtatgta gcttttgtt    1620 gcccgtggaa gggaagtgtt acactcccctt tagattaagc actttcaatt ttcgtaaatt    1680
gtgccaatgg caacatttta gattctcaga ggatgaagca tcctgttcca agtcttttt    1740 gattgtctag tagtcaatgg tatattgttg ttagtactgt agctgtctat tacaaaccta    1800
aaacagtgtt gcttctgtca tctattggaa tcgttatagt tattatattt agggatcagt    1860
gatggtgctg gattgaaata gagtgggcag tgatctgatt ttttaaaatg catatgttct    1920
aaaaaatcta atgagaaaat gttcctgcta tcaccatctt cttaatctt atttttcatag    1980 cacattatta tgcataatcg ccagccacag ttagtttatt gtctcgataa gtacagcagg    2040
cttaattaaa ataaagctgt aaataaatgc aaccaatgat aacacaattg taacgtaatt    2100
ccatagctta ttaatgtgat aaaagcaatt aataaaagac ctagccaacc cctttaacct    2160
cttaaataca ttattataga gttcatgcac aaacacatgc atctgagaat gtgtaaaagt    2220
tgttatatat cctcccaagg aaaaaaattg tgccttgaga gaaaggcaac gagatttaaa    2280
agatttgtgt ctataaccgt ctgttattag tattttatttt aacaaatata caccaccctt   2340
atccacacca attccttggt tgtttcttca acaattatc cacaagctttt ttaaagtttt   2400 tagaataatg ctattaagca gaccgatgca tacacaatca taaagtgaat tcttggtctg    2460 cccttttgtgg cgtctggaca atcataattc attcacatgt tgaatctcat aatttgtacc    2520 tatttttttcc catggtctaa cctcccactt acctcgaggt tgtatgtata tttctaagtt    2580
aggcaaatta aatctgattc ttatgatttg gttccgcagc ttataagata tgttaacttt    2640
tcttttgttt agattatgta taattagtct gatcttccat cccctcttt tttttttttt    2700
```

```
tactttaatt attttcaaat accttctttt aaaggtaaaa gcaatagtct tggaaaagcg    2760
aatctaccag caggggggcgc accagccaca tccctgaaac cagccgcgct gaaaagccgg   2820
tggccgcctt ctcttcccca gatcttctca acctttttctc tttcctaatc tccaggtccg   2880
tgtttacctt aatattacac ctggattaaa cagaaaacag tgctgtattt tgaagagcgc   2940
cgaatatgta tgcattttga gaaacccaat ctcacccttt ccgggttccc aagaactaaa   3000
acaagccata acttgagaga aaaggagaa ccttcggggg gcaggaaggt tgattggaaa    3060
taacttaagg aaagtctgca gaattctttt ttttacaact tttctgagtt tccagtgggt   3120
atatttagtg tgagtttgac agtaacaggc tagggagggc agagattgga gaaattgggg   3180
gtcgggggag tgattatggg aagaaggtta gtaaggaaca aaacaatgca ccgttttgta   3240
aagataataa atggaacgtg gctggtagat actattcagt acattttctt agggtgagta   3300
agggtagacc aggggaggag ggggcggaga gagtgttaca gaagaaagaa aataagtaac   3360
cctgatggtt taagcccttt ataaaaaaga aatggcatca ggttttttttt tctttattcc   3420 cccccacccc acccttttgta gtcaagtgca ttttagccac aaagatccca acaagagagt   3480
ggaaggaaac ttagacgagg ctttgtttga ctccgtgtag cgacaacaag agaaacaaaa   3540
ctacctattt gtaacggacg tgctgccatt gccctccgca ttgagcgcct acctattgaa   3600
atctttacgt cgggacaatg ggagagcggc taaaattacc ctcttgggtc ctgggcgggc   3660
aagattcctg agcccctacc cccgccccca tctcatcctc ctctaacccg ggccttgctg   3720 ggctcccct tccccagtcc cggccgcctt ctcccagtgt gcgctgcctg cacctgtgcc    3780
tggagagcat cgaccccgcc tcccaggcct tgagccctt tgcggcgcag ccccagcctt    3840
gcgcggcctg ggctttgcgg ccaccacaat ggaaatctac ggggaaaatg ccagggctgg   3900
ttctgctgga gtcctgggaa ctctgcgtgg gagggagttt gtgactgcgg cccaaaagcc   3960
acctccatac agtgccgtgg gatgccagga agttgaaatc accctccccc atcgcctgca   4020
cttttgagcg cccttccgtc tgtgtctttc cccagccccc atttgaaagc cgcacgaccg   4080 aaaccccttct tacggggagg catgggatgg gaatggggag tggggcaga cagtagaagc    4140 atcccctttg ctacggttga atgaagacag tctagtggga gatgtggctg gggctaagag   4200
gaagagctgc agtttcctgg gccaaagagc tgagttggac agggagatgg cagcttacca   4260
aggcctgctg gttctcagct ctagagtctg ccttatggtc cgagcaggat ttatttttaa   4320
gaacagagca agttacgtgg aagcaaggaa ggttttgagg acagaggttt gggtctccta   4380
acttctagtc gggactgtga aagggcgtg agagagtgtt ggcacctgta aggtaagaga    4440
ggagagcgga agagcgcagt acgggagcgg caccagaggg gctggagttg gggggagtg    4500 ctgtggatga gcgggagaac aatgacacac caactcctgc actggctgtt tccagaaata   4560
cgagttggac agccgccctg agccaccac tgtgccctgc cccaccccg caccttagct     4620 gcttcccgcg tcccatcctc atttaagtac cctgcaccaa aaagtaaatc aatattaagt   4680
ttaaagaaaa aaaacccac gtagtcttag tgctgtttac ccacttcctt cgaaaaggcg    4740
tgtggtgtga cctgttgctg cgagagggga tacaaaggtt tctcagtggc tggcaggctg   4800
gctctgggag cctcctcccc ctcctcgcct gccccctcct cccccggcct ccccgcgcg    4860 gccggcggcg cgggaggccc cgccccctttt catgcaaaac ccggcagcga ggctgggctc   4920
gagtggagga gccgccgcgc gctgattggt cgctagaaac ccatttattc cctgacagcc   4980
cccgtcacat ggatggttgt ctattaactt gttcaaaaaa gtatcaggag ttgtcaaggc   5040
agagaagaga gtgtttgcaa aaggggggaaa gtagtttgct gcctctttaa gactaggact   5100
```

-continued

```
gagagaaaga agaggagaga gaaagaaagg gagagaagtt tgagcccag gcttaagcct      5160 ttccaaaaaa taataataac aatcatcggc ggcggcagga tcggcagag gaggagggaa      5220 gcgcttttt tgatcctgat tccagtttgc ctctctcttt ttttccccca aattattctt      5280
cgcctgattt tcctcgcgga gccctgcgct cccgacaccc ccgcccgcct cccctcctcc      5340
tctccccccg cccgcgggcc ccccaaagtc ccggccgggc cgagggtcgg cggccgccgg      5400
cgggccgggc ccgcgcacag cgcccgcatg tacaacatga tggagacgga gctgaagccg      5460
ccggccccgc agcaaacttc gggggcggc ggcggcaact ccaccgcggc ggcggccggc      5520
ggcaaccaga aaacagccc ggaccgcgtc aagcggccca tgaatgcctt catggtgtgg      5580
tcccgcgggc agcggcgcaa gatggcccag gagaacccca agatgcacaa ctcggagatc      5640
agcaagcgcc tgggcgccga gtggaaactt ttgtcggaga cggagaagcg gccgttcatc      5700
gacgaggcta gcggctgcg agcgctgcac atgaaggagc acccggatta taaataccgg      5760
ccccggcgga aaaccaagac gctcatgaag aaggataagt acacgctgcc cggcgggctg      5820
ctggcccccg gcggcaatag catggcgagc ggggtcgggg tgggcgccgg cctgggcgcg      5880
ggcgtgaacc agcgcatgga cagttacgcg cacatgaacg gctggagcaa cggcagctac      5940
agcatgatgc aggaccagct gggctacccg cagcacccgg gcctcaatgc gcacggcgca      6000
gcgcagatgc agcccatgca ccgctacgac gtgagcgccc tgcagtacaa ctccatgacc      6060
agctcgcaga cctacatgaa cggctcgccc acctacagca tgtcctactc gcagcagggc      6120 accccctggca tggctcttgg ctccatgggt tcggtggtca agtccgaggc cagctccagc      6180 cccccctgtgg ttacctcttc ctcccactcc agggcgccct gccaggccgg ggacctccgg      6240
gacatgatca gcatgtatct ccccggcgcc gaggtgccgg aacccgccgc ccccagcaga      6300
cttcacatgt cccagcacta ccagagcggc ccggtgcccg gcacggccat taacggcaca      6360
ctgcccctct cacacatgtg agggccggac agcgaactgg aggggggaga aattttcaaa      6420
gaaaaacgag ggaaatggga ggggtgcaaa agaggagagt aagaaacagc atggagaaaa      6480
cccggtacgc tcaaaaagaa aaaggaaaaa aaaaatccc atcacccaca gcaaatgaca      6540
gctgcaaaag agaacaccaa tcccatccac actcacgcaa aaccgcgat gccgacaaga      6600 aaactttttat gagagagatc ctggacttct ttttggggga ctatttttgt acagagaaaa      6660
cctggggagg gtggggaggg cggggaatg gaccttgtat agatctggag gaaagaaagc      6720
tacgaaaaac tttttaaaag ttctagtggt acggtaggag ctttgcagga agtttgcaaa      6780
agtctttacc aataatattt agagctagtc tccaagcgac gaaaaaatg ttttaatatt      6840 tgcaagcaac ttttgtacag tatttatcga gataaacatg gcaatcaaaa tgtccattgt      6900
ttataagctg agaatttgcc aatattttc aaggagaggc ttcttgctga attttgattc      6960
tgcagctgaa atttaggaca gttgcaaacg tgaaaagaag aaaattattc aaatttggac      7020
attttaattg tttaaaaatt gtacaaaagg aaaaaattag aataagtact ggcgaaccat      7080
ctctgtggtc ttgttaaaaa agggcaaaag ttttagactg tactaaattt tataacttac      7140
tgttaaaagc aaaaatggcc atgcaggttg acaccgttgg taatttataa tagcttttgt      7200
tcgatcccaa ctttccattt tgttcagata aaaaaaacca tgaaattact gtgtttgaaa      7260 tatttttctta tggtttgtaa tatttctgta aattattgt gatattttaa ggttttcccc      7320
cctttatttt ccgtagttgt attttaaaag attcggctct gtattatttg aatcagtctg      7380
ccgagaatcc atgtatatat ttgaactaat atcatcctta taacaggtac attttcaact      7440
taagttttta ctccattatg cacagtttga gataaataaa ttttttgaaat atggacactg      7500
```

```
aaattattct tgagtctttc atttatttgg ataacactgt gattatacat aacttttcgg    7560
ggaattataa tactgtgctc agccaagaaa gcaaatacc  aaaaaccttg gtattactag    7620
tccagcatca tgtgctaatg ttaactgcaa aaagaaacg  gctggatgat taataagtac    7680
tggaaaaatt gaaatttctg tcatttctaa aatagaaact agagacatat attgtaaatc    7740
cgccccctcc ttttctaagc agcatgaata agcatgatgg ggacctatac ttaaaactga    7800
tttatgccac ttgttgccag aaaggattca attctgaaat ttttcatgta gtttagcaga    7860
tgggatattg agccaaatca gaaccaggtt ggctggtttt gttttcattt tcttcacagc    7920
acaatggccc tttgaaacct ggctatagag aaaaatgatg cttcttgtat cagaataatt    7980
gcaaactaga catgcaaagt gttcatctgc tgggtgggtg tttggattac tctggccctg    8040
ctattgtctg agaggaaaca agtggtttgc tttctttgtt ccttgacttc ataaactttc    8100
tcctctacat tttcctgttc ggggagaggg aaagaaaaga acatcttgca aaactccccg    8160
gcttatcata aacatagttt tttttattat ttattttctt ttttcccctc tctctccctc    8220
tctccctgaa ttccatttct taaattggca gcgcgggtcc aagcctgtag ccccaaatcg    8280
gataatctct gcagctgata acaagcaaaa gagaagccag gcaacagcca tattaaagaa    8340
gaaaacaatc aactctgagg tagatatttt actttgtccg gtctaatcac atttggagat    8400
gattatgctt tgatctgtt  aacaatgttt tactactgta gtagagaagt gggggagggg    8460
aaaggggtgg ggaaacaaga ttggatttgt tgtgtggtgg tttttttttt tttttttttt    8520
tttttttttt tttttttttt tttttttttt gccctaggaa aggtaaagaa aggctatagt    8580
tgtcctcagt gggagtggaa aagttgagac atcgccatgg tctttgaatt agcgatgctt    8640
ctgcatcacc acccacccct gctttggggc agcggataa  tctgttacct agtcagggac    8700
ttttctactt tatttactac ttgattcgct cgtcttcccc cacccacggg gaccaggaac    8760
caacaatcgg gcacttttaa gagcacgggg ttgcttccca caatttcaag agcttgtgtc    8820
aacttgctac aactttggag aagttggaat ccggcagcgt cttccaccct tgagtaaagt    8880
acccgctgca gccactaagt tagctcatcc cgttggtttg catcttctca tttccaagaa    8940
agtatttctt tctcatggtg ttgctaatgt tagttctggg ctgaactgag gatatctcat    9000
attttctgta ctttctattt ttttctagat tgctttgttt tagatatgta ctggttttta    9060
tttattactt ttttaatcct catttttagg ataacattgt actgggaagg gacaattatt    9120
attccagttc ccaattctaa gcaaggcatt ttccccccta attaatgcag agactctaaa    9180
agaatttccc ctagcctggc cagccattgt aatgcatata cggattattc acgtggtaat    9240
gagcacattc gccagttctt gctcacacat acgaataaaa gaaactttga ataaagatcc    9300
aaatgatcat cctgggggag tggggaggat attcccggaa tttgaggcag tcaaatatat    9360
agattatata tattttgaaa atagaaatat attagaaata tgtatagagg tttacagtaa    9420
ttgcactgca ctcacctctc atttttttaaa aaaagccca  cagggtcagc aacttctgg    9480 caaaatggtc aggttcaaat att                                           9503
```

<210> SEQ ID NO 2
<211> LENGTH: 2283
<212> TYPE: DNA
<213> ORGANISM: Mus musculus

<400> SEQUENCE: 2

```
gtgtttgcaa aaagggaaaa gtactttgct gcctctttaa gactagggct gggagaaaga     60
agaggagaga gaaagaaagg agagaagttt ggagcccgag gcttaagcct ttccaaaaac    120
```

| | |
|---|---|
| taatcacaac aatcgcggcg gcccgaggag gagagtctcc ctgttttttc atcccaattg | 180 |
| cacttcgccc gtctcgagct ccgcttcccc ccaactattc tccgccagat ctccgcgcag | 240 |
| ggccgtgcac gccgaggccc ccgccgcgcg cccctgcatc ccggcccccg agcgcggccc | 300 |
| ccacagtccc ggccgggccg agggttggcg gccgccggcg ggccgcccgc ccagcgcccg | 360 |
| catgtataac atgatggaga cggagctgaa gccgccgggc ccgcagcaag cttcgggggg | 420 |
| cggcggcgga ggaggcaacg ccacggcggc ggcgaccggc ggcaaccaga agaacagccc | 480 |
| ggaccgcgtc aagaggccca tgaacgcctt catggtatgg tcccgggggc agcggcgtaa | 540 |
| gatggcccag gagaacccca agatgcacaa ctcggagatc agcaagcgcc tgggcgcgga | 600 |
| gtggaaactt ttgtccgaga ccgagaagcg gccgttcatc gacgaggcca agcggctgcg | 660 |
| cgctctgcac atgaaggagc acccggatta taaataccgg ccgcggcgga aaaccaagac | 720 |
| gctcatgaag aaggataagt acacgcttcc cggaggcttg ctggccccg gcgggaacag | 780 |
| catggcgagc ggggttgggg tgggcgccgg cctgggtggc gggctgaacc agcgcatgga | 840 |
| cagctacgcg cacatgaacg gctggagcaa cggcagctac agcatgatgc aggagcagct | 900 |
| gggctacccg cagcacccgg gcctcaacgc tcacggcgcg gcacagatgc aaccgatgca | 960 |
| ccgctacgtc gtcagcgccc tgcagtacaa ctccatgacc agctcgcaga cctacatgaa | 1020 |
| cggctcgccc acctacagca gtcctactc gcagcagggc accccggta tggcgctggg | 1080 |
| ctccatgggc tctgtggtca gtccgaggc cagctccagc ccccccgtgg ttacctcttc | 1140 |
| ctcccactcc agggcgccct gccaggccgg ggacctccgg gacatgatca gcatgtacct | 1200 |
| ccccggcgcc gaggtgccgg agcccgctgc gcccagtaga ctgcacatgg cccagcacta | 1260 |
| ccagagcggc ccggtgcccg gcacggccaa atacggcaca ctgcccctgt cgcacatgtg | 1320 |
| agggctggac tgcgaactgg agaagggag agattttcaa agagatacaa gagaattggg | 1380 |
| aggggtgcaa aaagaggaga gtaggaaaaa tctgataatg cycaaaagga aaaaaccac | 1440 |
| caatcccatc caaattaacg cttttttcggt gatgccgact agaaaacttt tatgagagat | 1500 |
| ctggaggaaa aaaactacgc aaaacttttt tttaaagttc tagtggtacg ttaggcgctt | 1560 |
| cgcagggagt tcgcaaaagt cttttaccagt aatatttaga gctagactcc gggcgatgaa | 1620 |
| aaaaaagttt taatatttgc aagcaacttt tgtacagtat ttatcgagat aaacatggca | 1680 |
| atcaaatgtc cattgtttat aagctgagaa tttgccaata ttttttcgagg aaagggaaca | 1740 |
| agctgggaaa agattctgca gttaaattta ggaccgttac aaacaaggaa ggagtttatt | 1800 |
| cggatttgaa cattttagtt ttaaaattgt acaaaaggaa aacatgagag caagtactgg | 1860 |
| caagaccgtt ttcgtggtct tgtttaaggc aaacgttcta gattgtagta aattttaac | 1920 |
| ttactgttaa aggcaaaaaa aaaatgccca tgcaggttga tatcgttggt aatttataat | 1980 |
| agcttttgtt caatcctacc cttttcatttt gttcacataa aaaatatgga attactgtgt | 2040 |
| ttgaaatatt ttcttatggt ttgtaatatt tctgtaaatt gtgatatttt aaggtttttc | 2100 |
| ccccctttta ttttccgtag ttgtatttta aaagattcgg ctctcttatt ggaatcaggc | 2160 |
| tggcgagaat ccatgtatat atttgaacta ataccatcct tataacagct acattttcgg | 2220 |
| cttaagtttt tactccatta tgcacagttt gagataaata aattttgaa atatggacac | 2280 |
| tga | 2283 |

<210> SEQ ID NO 3
<211> LENGTH: 317
<212> TYPE: PRT
<213> ORGANISM: Homo sapiens

<400> SEQUENCE: 3

```
Met Tyr Asn Met Met Glu Thr Glu Leu Lys Pro Pro Gly Pro Gln Gln
  1               5                  10                  15
Thr Ser Gly Gly Gly Gly Asn Ser Thr Ala Ala Ala Gly Gly
             20                  25                  30
Asn Gln Lys Asn Ser Pro Asp Arg Val Lys Arg Pro Met Asn Ala Phe
             35                  40                  45
Met Val Trp Ser Arg Gly Gln Arg Arg Lys Met Ala Gln Glu Asn Pro
 50                  55                  60
Lys Met His Asn Ser Glu Ile Ser Lys Arg Leu Gly Ala Glu Trp Lys
 65                  70                  75                  80
Leu Leu Ser Glu Thr Glu Lys Arg Pro Phe Ile Asp Glu Ala Lys Arg
                 85                  90                  95
Leu Arg Ala Leu His Met Lys Glu His Pro Asp Tyr Lys Tyr Arg Pro
                100                 105                 110
Arg Arg Lys Thr Lys Thr Leu Met Lys Lys Asp Lys Tyr Thr Leu Pro
                115                 120                 125
Gly Gly Leu Leu Ala Pro Gly Gly Asn Ser Met Ala Ser Gly Val Gly
130                 135                 140
Val Gly Ala Gly Leu Gly Ala Gly Val Asn Gln Arg Met Asp Ser Tyr
145                 150                 155                 160
Ala His Met Asn Gly Trp Ser Asn Gly Ser Tyr Ser Met Met Gln Asp
                165                 170                 175
Gln Leu Gly Tyr Pro Gln His Pro Gly Leu Asn Ala His Gly Ala Ala
                180                 185                 190
Gln Met Gln Pro Met His Arg Tyr Asp Val Ser Ala Leu Gln Tyr Asn
                195                 200                 205
Ser Met Thr Ser Ser Gln Thr Tyr Met Asn Gly Ser Pro Thr Tyr Ser
                210                 215                 220
Met Ser Tyr Ser Gln Gln Gly Thr Pro Gly Met Ala Leu Gly Ser Met
225                 230                 235                 240
Gly Ser Val Val Lys Ser Glu Ala Ser Ser Pro Pro Val Val Thr
                245                 250                 255
Ser Ser Ser His Ser Arg Ala Pro Cys Gln Ala Gly Asp Leu Arg Asp
                260                 265                 270
Met Ile Ser Met Tyr Leu Pro Gly Ala Glu Val Pro Glu Pro Ala Ala
                275                 280                 285
Pro Ser Arg Leu His Met Ser Gln His Tyr Gln Ser Gly Pro Val Pro
                290                 295                 300
Gly Thr Ala Ile Asn Gly Thr Leu Pro Leu Ser His Met
305                 310                 315

<210> SEQ ID NO 4
<211> LENGTH: 319
<212> TYPE: PRT
<213> ORGANISM: Mus musculus

<400> SEQUENCE: 4

Met Tyr Asn Met Met Glu Thr Glu Leu Lys Pro Pro Gly Pro Gln Gln
  1               5                  10                  15
Ala Ser Gly Gly Gly Gly Gly Gly Asn Ala Thr Ala Ala Ala Thr
             20                  25                  30
Gly Gly Asn Gln Lys Asn Ser Pro Asp Arg Val Lys Arg Pro Met Asn
             35                  40                  45
```

Ala Phe Met Val Trp Ser Arg Gly Gln Arg Lys Met Ala Gln Glu
 50                  55                  60

Asn Pro Lys Met His Asn Ser Glu Ile Ser Lys Arg Leu Gly Ala Glu
 65                  70                  75                  80

Trp Lys Leu Leu Ser Glu Thr Glu Lys Arg Pro Phe Ile Asp Glu Ala
                 85                  90                  95

Lys Arg Leu Arg Ala Leu His Met Lys Glu His Pro Asp Tyr Lys Tyr
            100                 105                 110

Arg Pro Arg Arg Lys Thr Lys Thr Leu Met Lys Lys Asp Lys Tyr Thr
        115                 120                 125

Leu Pro Gly Gly Leu Leu Ala Pro Gly Gly Asn Ser Met Ala Ser Gly
    130                 135                 140

Val Gly Val Gly Ala Gly Leu Gly Gly Leu Asn Gln Arg Met Asp
145                 150                 155                 160

Ser Tyr Ala His Met Asn Gly Trp Ser Asn Gly Ser Tyr Ser Met Met
                165                 170                 175

Gln Glu Gln Leu Gly Tyr Pro Gln His Pro Gly Leu Asn Ala His Gly
            180                 185                 190

Ala Ala Gln Met Gln Pro Met His Arg Tyr Val Val Ser Ala Leu Gln
        195                 200                 205

Tyr Asn Ser Met Thr Ser Ser Gln Thr Tyr Met Asn Gly Ser Pro Thr
    210                 215                 220

Tyr Ser Met Ser Tyr Ser Gln Gln Gly Thr Pro Gly Met Ala Leu Gly
225                 230                 235                 240

Ser Met Gly Ser Val Val Lys Ser Glu Ala Ser Ser Ser Pro Pro Val
                245                 250                 255

Val Thr Ser Ser His Ser Arg Ala Pro Cys Gln Ala Gly Asp Leu
            260                 265                 270

Arg Asp Met Ile Ser Met Tyr Leu Pro Gly Ala Glu Val Pro Glu Pro
        275                 280                 285

Ala Ala Pro Ser Arg Leu His Met Ala Gln His Tyr Gln Ser Gly Pro
    290                 295                 300

Val Pro Gly Thr Ala Lys Tyr Gly Thr Leu Pro Leu Ser His Met
305                 310                 315

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gacctagcca gaccccctta                                              20

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
agataagtgg gaggttaagc gagg                                         24

<210> SEQ ID NO 7
<211> LENGTH: 20
<212> TYPE: DNA
<213> ORGANISM: Artificial Sequence

```
<220> FEATURE:
<223> OTHER INFORMATION: Primer

<400> SEQUENCE: 7
cgttggctac ccgtgatatt                                              20

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gtgagacgtg ctacttccat ttgtc                                        25

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
aggctgagtc gggtcaatta                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gacctagcca gaccccctta                                              20

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
agataagtgg gaggttaagc gagg                                         24

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cgttggctac ccgtgatatt                                              20

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
gtgagacgtg ctacttccat ttgtc                                        25
```

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
aggctgagtc gggtcaatta                                              20
```